US010912620B2

(12) United States Patent
Mahoney et al.

(10) Patent No.: US 10,912,620 B2
(45) Date of Patent: Feb. 9, 2021

(54) SNARE TOOL MANIPULATOR SYSTEM

(71) Applicant: VANDERBILT UNIVERSITY, Nashville, TN (US)

(72) Inventors: Arthur W. Mahoney, Nashville, TN (US); Patrick L. Anderson, Nashville, TN (US); Robert J. Webster, III, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 230 days.

(21) Appl. No.: 16/067,621

(22) PCT Filed: Jan. 6, 2017

(86) PCT No.: PCT/US2017/012599
§ 371 (c)(1),
(2) Date: Jul. 2, 2018

(87) PCT Pub. No.: WO2017/120516
PCT Pub. Date: Jul. 13, 2017

(65) Prior Publication Data
US 2019/0015166 A1    Jan. 17, 2019

Related U.S. Application Data

(60) Provisional application No. 62/275,480, filed on Jan. 6, 2016, provisional application No. 62/279,063, filed on Jan. 15, 2016.

(51) Int. Cl.
*A61B 17/29* (2006.01)
*A61B 34/00* (2016.01)
(Continued)

(52) U.S. Cl.
CPC ............ *A61B 34/70* (2016.02); *A61B 17/221* (2013.01); *A61B 17/32056* (2013.01);
(Continued)

(58) Field of Classification Search
CPC ... A61B 17/221; A61B 17/29; A61B 17/2909; A61B 17/3205; A61B 17/32056;
(Continued)

(56) References Cited

U.S. PATENT DOCUMENTS

| 2002/0188262 | A1  | 12/2002 | Abe |
| 2013/0190775 | A1* | 7/2013 | Piligian .............. A61B 17/0218 606/130 |
| 2015/0150634 | A1* | 6/2015 | Isoda ..................... A61B 34/30 606/130 |

FOREIGN PATENT DOCUMENTS

| IE | 20 030 158 A1 | 10/2003 |
| WO | 2012/035524 A2 | 3/2012 |

OTHER PUBLICATIONS

International Search Report and Written Opinion dated May 24, 2017 for corresponding International Application No. PCT/US2017/012599.

* cited by examiner

*Primary Examiner* — Vi X Nguyen
(74) *Attorney, Agent, or Firm* — Tarolli, Sundheim, Covell & Tummino LLP

(57) ABSTRACT

A snare tool manipulator system includes an elongated flexible device having a length and including a distally mounted end effector configured to perform a task. The flexible device is operable to manipulate the end effector in order to perform the task. The system also includes an elongated snare tool including a distally mounted snare device configured for grasping the flexible elongated member at a position along its length. The snare tool is operable robotically to manipulate the flexible device which in response manipulates the end effector.

24 Claims, 14 Drawing Sheets

(51) Int. Cl.
*A61B 17/221* (2006.01)
*A61B 17/3205* (2006.01)
*A61B 34/20* (2016.01)
*A61B 34/30* (2016.01)
*A61B 90/50* (2016.01)
*A61B 17/00* (2006.01)
*A61B 17/22* (2006.01)

(52) U.S. Cl.
CPC .............. *A61B 34/20* (2016.02); *A61B 34/30* (2016.02); *A61B 90/50* (2016.02); *A61B 2017/00358* (2013.01); *A61B 2017/00867* (2013.01); *A61B 2017/2212* (2013.01); *A61B 2017/22035* (2013.01); *A61B 2034/301* (2016.02)

(58) Field of Classification Search
CPC . A61B 2017/292; A61B 17/28; A61B 17/282; A61B 2017/00358; A61B 2017/2926
See application file for complete search history.

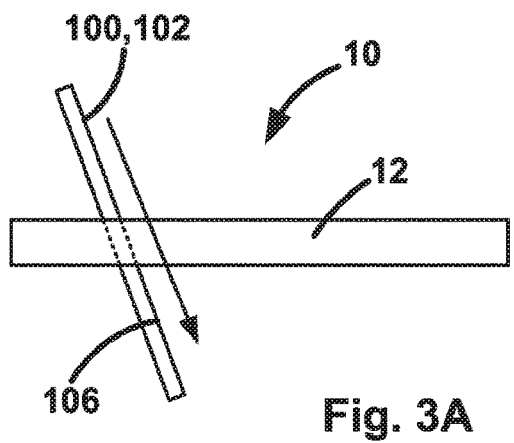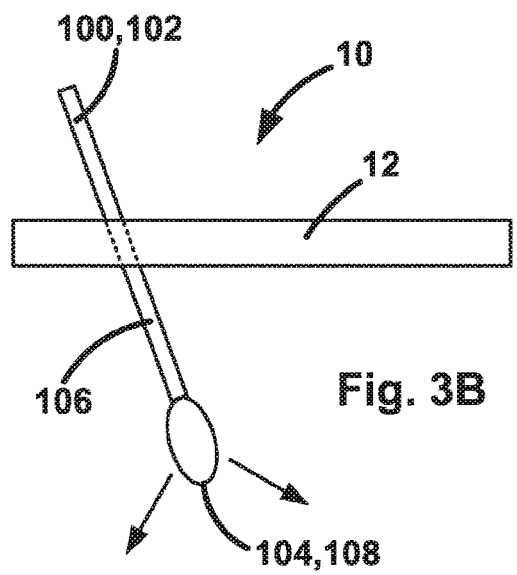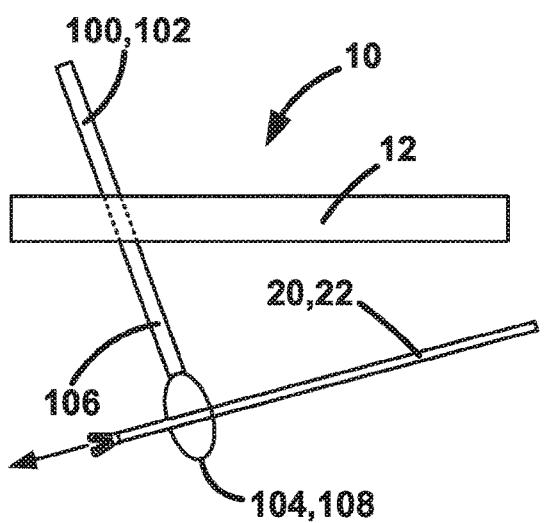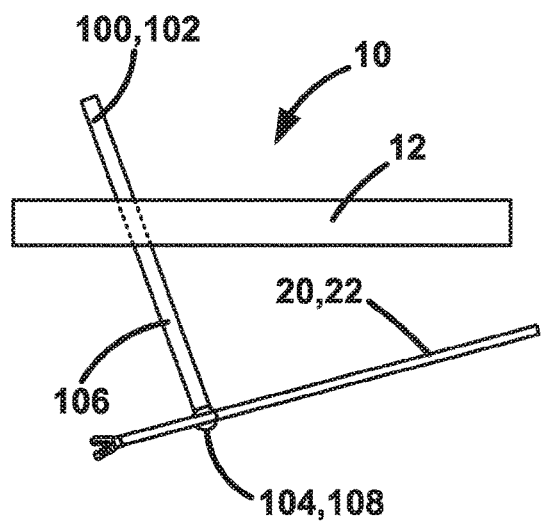

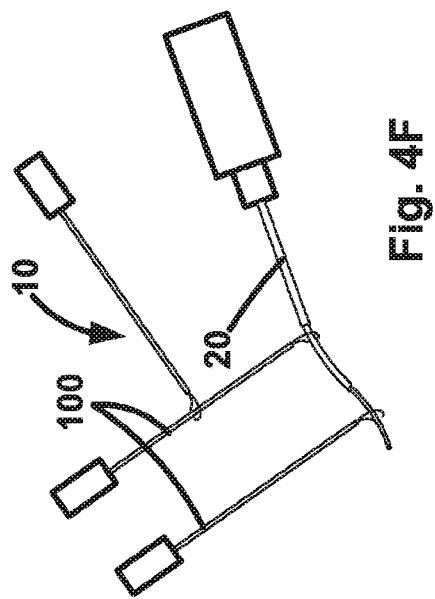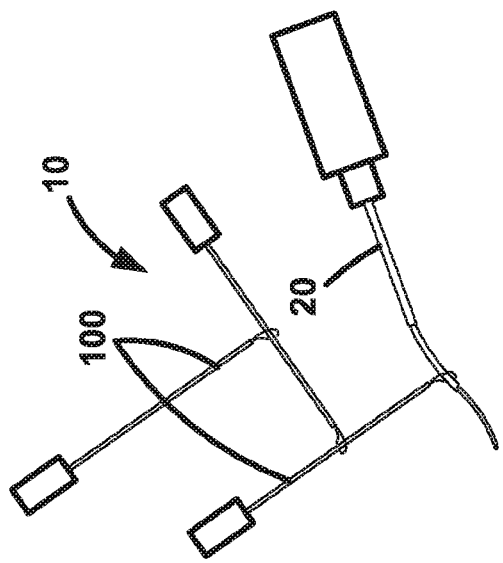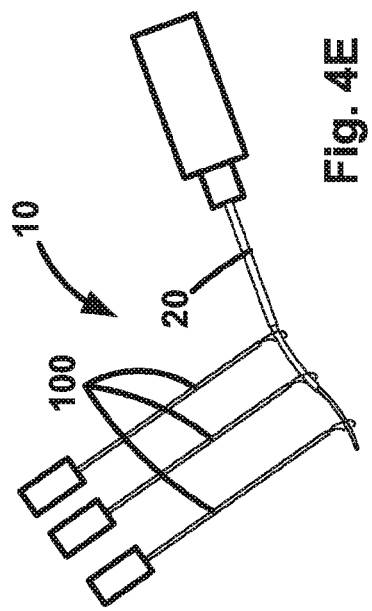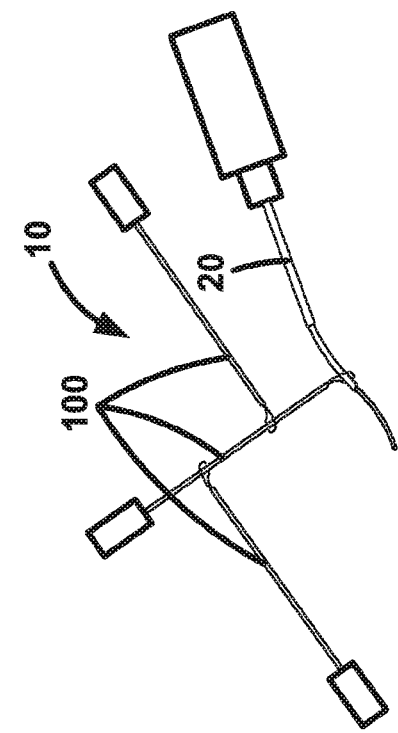

SNARE TOOL MANIPULATOR SYSTEM

RELATED APPLICATIONS

This application claims the benefit of U.S. Provisional Application Ser. No. 62/275,480, filed Jan. 6, 2015 and U.S. Provisional Application Ser. No. 62/279,063, filed Jan. 15, 2015.

GOVERNMENT FUNDING

This invention was made with government support under grant numbers EB017467 and EB017952 awarded by the National Institutes of Health and under grant number 1054331 awarded by the National Science Foundation. The government has certain rights in the invention.

TECHNICAL FIELD

The invention relates generally to manipulator systems actuated robotically, manually, or a combination of robotically and manually, that employ the use of one or more flexible devices for navigating with dexterity. In particular, the invention relates to the use of snare tools for helping to support and manipulate a flexible device.

BACKGROUND

Manually and robotically operated flexible devices for navigating complex structures are being used with increasing popularity. Continuum devices or manipulators are robotic devices that are continuous in form and can be actuated to bend at any point along its length, much like a snake's body or elephant's trunk. Continuum devices are excellent at navigating complex spaces to position end effectors (tools, lights, lasers, cameras, etc.) at a desired location. Depending on their configuration and construction, continuum devices may not be ideal in exerting force via the end effector. Additionally, continuum devices do exhibit limitations in terms of dexterity or navigational capability.

One field in which flexible devices can be particularly useful is the field of surgery, particularly minimally invasive surgical procedures. Under current approaches, flexible device are deployed through a single port into a patient's body. This single port approach comes at the cost of a larger entry port and incision, without definitive clinical benefit. Additionally, under the single port approach, all of the support for the flexible device must reside in the structure outside the patient at the single entry point. As a result, navigating to more remote surgical sites in the patient can make supporting the flexible device more challenging as the surgical site becomes more remote from the incision and as the manipulation forces required at the site increase. This can be especially challenging where the flexible device is a small diameter (e.g., needle-like) robotically operated continuum device, which is susceptible to the influence of force exerting structures contacting the device.

SUMMARY

The invention relates to a system that implement a flexible device, such as a continuum device, and one or more snare tools for helping to support and/or manipulate the flexible device. The snare tools include an end effector (e.g., a snare loop, hook, grasper, etc.) configured to snare or otherwise grasp the flexible device in order to provide the desired support and/or manipulation of the flexible device. In doing so, the snare tools move the support for the flexible device, at least partially, from the flexible device itself to the location where the snare tool grasps the flexible device. The flexible device and/or snare tools can be rigid or flexible, straight or curved, and manually or robotically operated. In one implementation, the flexible device can be a continuum device actuated robotically or manually. In another implementation, the snare tools can be continuum devices actuated robotically or manually.

The snare tools can be actuated or otherwise manipulated, robotically and/or by hand, to produce various responses from the flexible device. The snare tools can push, pull, rotate the flexible device about its longitudinal axis, bend the flexible device, twist the flexible device transverse to its longitudinal, translate the flexible device along its longitudinal axis to advance or retract the flexible device, or impart any other motion or manipulation that could be applied by hand. This makes the system particularly adept at providing a high degree of dexterity in locations where manual access is impracticable or impossible.

According to one aspect, the system can be a surgical system implementing a flexible device for performing percutaneous surgical procedures. For example, the flexible device can be a small diameter (i.e., needle-sized) flexible device, such as a manually steerable flexible endoscope, a steerable catheter, a steerable instrument delivered by wire or cable (e.g., for delivering illumination, video camera, electrode, a probe, tool, etc.). The flexible device could, for example, be a tube or wire constructed from a nickel-titanium ("Nitinol") alloy. As another example, the flexible device can be a continuum device, such as a robotic continuum device.

The flexible device is delivered surgically through an extremely small incision or no incisions at all (i.e., via puncture insertion). In one particular example, the flexible device can be a robotic continuum device. A robotic continuum device can take the form of a concentric tube manipulator, which includes multiple pre-curved superelastic (e.g., nickel-titanium "nitinol") tubes that are nested concentrically and that are translatable telescopically and rotatable relative to each other in order to navigate the patient anatomy and maneuver the tip of the continuum device to a surgical site. The robotic continuum device can have alternative configurations, such as the recently developed "elephant trunk" type robotic devices with multiple axially aligned actuatable joints. The tip of the continuum device is outfitted with an end effector, such as a surgical instrument or tool, that is configured to perform the specific surgical procedure for which the continuum device is tasked.

The surgical system also includes one or more snare tools that delivered surgically into the patient's body at locations different from that at which the flexible device is delivered. The snare tools themselves can be needle-like structures that can be delivered through extremely small incisions or through puncture insertion. The snare tools grasp the flexible device inside the patient and provide a means by which to percutaneously support and manipulate the flexible device from outside the patient. In doing so, the snare tools move the support for the flexible device from the remote insertion point of the flexible device to the location where the snare tool grasps the device.

In one example configuration, the snare tool includes a snare tube/needle and a flexible (e.g., wire) snare that extends through the tube. The snare tube is inserted through the patient's skin and the snare is deployed from the tube tip. A flexible device, such as a continuum device, is navigated through the open snare, and the snare is closed onto the flexible device to grasp the same. Thereafter, operation of the flexible device can itself be operated in its normal fashion, with the snare needle providing a support structure against which the continuum device can act. Additionally or alternatively, the snare tool can be used to manipulate the flexible device. This manipulation of the flexible device by the snare tool can be used to achieve motion not otherwise achievable through operation of the flexible device alone.

Through this design, the system disclosed herein can possess the characteristics of several systems. The system can possess continuum device characteristics in that a continuum device can be implemented as the primary flexible device. The system can also possess parallel robotic characteristics in that the snare tools can act as linear actuators much in the manner that of those implemented in robotic kinematic systems, such as Stewart platform positioning systems. Furthermore, by implementing the snare tools, the flexible device can be reconfigured to perform functions it would otherwise be incapable of performing. For example, the snare tools, implemented to form a parallel actuating structure, can allow the flexible device to perform functions requiring the exertion of forces that the flexible device would otherwise be incapable of providing.

Snare Tool Manipulator System

The invention can relate to a snare tool manipulator system includes an elongated flexible device having a length and including a distally mounted end effector configured to perform a task. The flexible device is operable to manipulate the end effector in order to perform the task. The system also includes an elongated snare tool including a distally mounted snare device configured for grasping the flexible elongated member at a position along its length. The snare tool is operable robotically to manipulate the flexible device which in response manipulates the end effector.

According to one aspect, alone or in combination with any other aspect, the snare tool can include a snare tube for delivering the snare device. The snare tool can also include a snare actuating member that extends through an inner lumen of the snare tube and is actuatable to operate the snare device.

According to another aspect, alone or in combination with any other aspect, the snare actuating member can include a snare wire that extends through the inner lumen of the snare tube. The snare device can include a looped portion of the snare wire. The snare wire can be actuatable to extend the snare loop from the distal end of the snare tube to receive the flexible device and retract the snare loop into the distal end of the snare tube.

According to another aspect, alone or in combination with any other aspect, the snare device can include at least one of a loop, a hook, and a grasper.

According to another aspect, alone or in combination with any other aspect, the snare tube can be configurable to include at least one of straight sections and curved sections.

According to another aspect, alone or in combination with any other aspect, the snare tube can be a needle-like structure having a diameter of 3.0 millimeters or less.

According to another aspect, alone or in combination with any other aspect, the snare device can include a loop and the snare tool can be configured to position the loop for receiving the flexible device and permitting the flexible device to pass through the loop. The snare tool can be actuatable to cause the loop to constrict onto and grasp the flexible device.

According to another aspect, alone or in combination with any other aspect, the snare actuating member can include a wire constructed of a material with shape memory properties and the snare device can include a looped portion of the wire that has a predetermined shape. The looped portion can be adapted to be compressed when it is passed through the inner lumen of the snare tube and to resume its predetermined shape when it exits through the distal end of the snare tube.

According to another aspect, alone or in combination with any other aspect, the predetermined shape of the looped portion can be circular, elliptical, polygonal, or P shape.

According to another aspect, alone or in combination with any other aspect, the snare tool can be adapted to actuate the end effector of the flexible device by applying a rotational force to the end effector.

According to another aspect, alone or in combination with any other aspect, the snare tool manipulator system can include snare tool actuator for robotically actuating the snare tool, a flexible tool actuator for robotically actuating the flexible tool, a controller programmed to control the snare tool actuator and flexible tool actuator according to received operator instructions in order to produce desired movement of the end effector on the distal end of the flexible tool, and a user interface including a graphical user interface and a control input device. The control input device can be configured to provide the user instructions to the controller in response to control inputs from the user indicative of the desired movement of the end effector.

According to another aspect, alone or in combination with any other aspect, the controller can be programmed to implement a kinematic model to estimate a topology of the flexible tool and snare tool combination, perform a calculation to determine the motion of the snare tool actuator and the flexible tool actuator necessary to produce the desired movement of the end effector indicated by the control inputs, and actuate the snare tool actuator and flexible tool actuator to produce the desired movement of the end effector.

According to another aspect, alone or in combination with any other aspect, the controller can be further programmed to perform a simulation using the kinematic model to determine whether the desired movement of the end effector is possible with the current topology of the flexible tool and snare tool, and to adjust the configuration of the snare tool in order to produce a topology of the flexible tool and snare tool that will permit the desired movement of the end effector.

According to another aspect, alone or in combination with any other aspect, the controller can be further programmed to iterate the determination of whether the desired movement of the end effector is possible and the adjustment of the configuration of the snare tool until a topology of the flexible tool and snare tool that will permit the desired movement of the end effector is determined.

According to another aspect, alone or in combination with any other aspect, the controller can be programmed to enforce a remote center of motion of the snare tool when actuating the snare tool actuator.

According to another aspect, alone or in combination with any other aspect, the snare tool actuator can include a robotic arm.

According to another aspect, alone or in combination with any other aspect, the system can include a tracking system for tracking the position and orientation of the snare tool and providing the tracked position and orientation to the controller.

According to another aspect, alone or in combination with any other aspect, the flexible tool can include a continuum device.

According to another aspect, alone or in combination with any other aspect, the flexible device can include a surgical device for percutaneously delivering the end effector to a worksite in order to perform a surgical task. The snare tool can be configured for percutaneous insertion to grasp and manipulate the flexible device.

According to another aspect, alone or in combination with any other aspect, the system can include a snare tool actuator for robotically actuating the snare tool. The snare tool actuator can be configured to be static in position relative to the patient.

According to another aspect, alone or in combination with any other aspect, the system can include a snare tool actuator for robotically actuating the snare tool. The snare tool actuator can be adapted to have a dynamically controlled position so that is moves in response to patient movement in order to maintain a fixed position relative to the patient.

According to another aspect, alone or in combination with any other aspect, the system can include sensors for sensing the position of the snare tool relative to a predetermined location relative to the patient.

According to another aspect, alone or in combination with any other aspect, the snare tool can be configured to be patient mounted in order to maintain a fixed position relative to the patient.

Surgical Method

The invention can also relate to a method for performing surgery on a patient. The method can include inserting an elongated flexible surgical tool comprising a distally located end effector into the patient's body percutaneously or through a natural orifice. The method can also include providing an elongated snare tool comprising a distally located snare device, inserting the snare tool percutaneously into the patient's body, and actuating the snare device to grasp the surgical tool.

According to one aspect, alone or in combination with any other aspect, the method can also include actuating the snare tool to manipulate the surgical tool.

According to another aspect, alone or in combination with any other aspect, the method can also include positioning the distal end of the snare tool in the patient's body, guiding the surgical tool to a desired location relative to the snare tool, and actuating the snare device in order to grasp the surgical tool.

According to another aspect, alone or in combination with any other aspect, the method can also include guiding the snare tool to a desired location relative to the surgical tool and actuating the snare device in order to grasp the surgical tool.

According to another aspect, alone or in combination with any other aspect, the snare device can include a snare loop that is extendable from and retractable into the distal end of the snare tool. The method can also include positioning the distal end of the snare tool in the patient's body, extending the snare loop from the distal end of the snare tool, guiding the surgical tool through the extended snare loop, and retracting the snare loop into the snare tool in order to grasp the surgical tool.

According to another aspect, alone or in combination with any other aspect, the snare device can include a snare tube and a snare member that extends through the snare loop and is configured to actuate the snare device. The method can also include applying tension to the snare member in order to actuate the snare device.

According to another aspect, alone or in combination with any other aspect, providing a snare tool can include providing a plurality of snare tools. Inserting the snare tool can include inserting the plurality of snare tools percutaneously into the patient's body. Actuating the snare device can include actuating snare devices of the plurality of snare tools to grasp the surgical tool.

According to another aspect, alone or in combination with any other aspect, the method can also include actuating at least one of the snare devices to grasp one of the plurality of snare tools.

According to another aspect, alone or in combination with any other aspect, the method can also include actuating at least two of the snare devices to grasp the surgical tool at the same location.

According to another aspect, alone or in combination with any other aspect, the method can also include positioning at least two of the snare tools to grasp the surgical tool in parallel.

According to another aspect, alone or in combination with any other aspect, the method can also include providing a user interface, providing a controller, configuring the controller to receive from the user interface operator instructions regarding indicative of desired movement of the distally located end effector of the surgical tool, and configuring the controller to robotically actuate the snare tool and the surgical tool in response to the operator instructions in order to produce the desired movement of the end effector on the distal end of the surgical tool.

According to another aspect, alone or in combination with any other aspect, the method can also include programming the controller to implement a kinematic model to estimate a topology of the surgical tool and snare tool combination, performing a calculation to determine the motion of the snare tool and the flexible tool necessary to produce the desired movement of the end effector indicated by the control inputs, and robotically actuating the snare tool and surgical tool to produce the desired movement of the end effector.

According to another aspect, alone or in combination with any other aspect, the method can also include programming the controller to perform a simulation using the kinematic model to determine whether the desired movement of the end effector is possible with the current topology of the surgical tool and snare tool, and to adjust the configuration of the snare tool in order to produce a topology of the surgical tool and snare tool that will permit the desired movement of the end effector.

According to another aspect, alone or in combination with any other aspect, the method can also include programming the controller to iterate the determination of whether the desired movement of the end effector is possible and the adjustment of the configuration of the snare tool until a topology of the surgical tool and snare tool that will permit the desired movement of the end effector is determined.

According to another aspect, alone or in combination with any other aspect, the method can also include tracking the position and orientation of the snare tool and providing the tracked position and orientation to the controller.

According to another aspect, alone or in combination with any other aspect, providing a snare tool can include providing a rigid snare tool. Robotically actuating the snare tool can include actuating a robotic arm supporting the snare tool to maneuver the rigid snare tool while enforcing a remote center of motion of the snare tool.

Control Algorithm

The invention can also relate to a method for controlling a system including a robotically actuated flexible tool and a robotically actuated snare tool that grasps the flexible tool, wherein the flexible tool and snare tool are robotically actuatable to manipulate an end effector distally mounted on the flexible tool. The method can include receiving control inputs indicative of desired movements of the end effector, applying a kinematic model to estimate a topology of the flexible tool and snare tool combination, performing a calculation to determine the motion of the snare tool and the flexible tool necessary to produce the desired movement of the end effector indicated by the control inputs, and robotically actuating the snare tool and flexible tool to produce the desired movement of the end effector.

According to one aspect, alone or in combination with any other aspect, the method can also include performing a simulation using the kinematic model to determine whether the desired movement of the end effector is possible with the current topology of the flexible tool and snare tool.

According to another aspect, alone or in combination with any other aspect, the method can also include adjusting the configuration of the snare tool in order to produce a topology of the flexible tool and snare tool that will permit the desired movement of the end effector.

According to another aspect, alone or in combination with any other aspect, the method can also include iterating the determination of whether the desired movement of the end effector is possible and adjusting the configuration of the snare tool until a topology of the flexible tool and snare tool that will permit the desired movement of the end effector is determined.

According to another aspect, alone or in combination with any other aspect, the method can also include tracking the position and orientation of the snare tool and controlling the actuation of the snare tool to enforce a remote center of motion of the snare tool in response to the tracked position and orientation of the snare tool.

According to another aspect, alone or in combination with any other aspect, the flexible tool can include a concentric tube manipulator comprising a plurality of nested, concentric tubes, at least one of which has a pre-curved elastic configuration, an innermost one of the concentric tubes carrying the end effector. Robotically actuating the flexible tool can included robotically imparting at least one of rotation and translation of one or more of the concentric tubes relative to each other to manipulate the end effector.

According to another aspect, alone or in combination with any other aspect, providing a snare tool can include providing a rigid snare tool. Robotically actuating the snare tool can include actuating a robotic arm supporting the snare tool to maneuver the rigid snare tool while enforcing a remote center of motion of the snare tool.

According to another aspect, alone or in combination with any other aspect, the method can also include providing a user interface, providing a controller, configuring the controller to receive from the user interface operator instructions regarding indicative of desired movement of the distally located end effector of the flexible tool, and configuring the controller to robotically actuate the snare tool and the flexible tool in response to the operator instructions in order to produce the desired movement of the end effector on the distal end of the flexible tool.

DRAWINGS

FIGS. 3A-3D are magnified views of a portion of the system of FIG. 2.

FIGS. 4A-4J illustrate different configurations of a portion of the system of FIGS. 1-3.

DESCRIPTION

A system includes a flexible device and one or more snare tools for helping to manipulate the flexible device. The flexible device can be any flexible device including an end effector and configured to be navigable in order to deliver the end effector to a worksite in order to perform a desired function. The snare tool(s) are equipped with end effectors, such as hooks or snare tools, configured to grasp onto the flexible device. The snare tool, grasping the flexible device, can be used to help support, position, maneuver, or otherwise control the grasped flexible device.

The flexible device can have a variety of configurations. The flexible device can be any flexible elongated member that can be manually or robotically operated to deliver an end effector to a worksite. For example, the flexible device can be configured as a flexible tube, rod, wire, or cable. The flexible device could, for example, be a tube or wire constructed from a nickel-titanium ("Nitinol") alloy. The flexible device can also be what is referred to as a continuum device, which are dexterous flexible elongated members that are actuatable remotely, mechanically and/or robotically, to control its motion in a manner similar to which a snake or elephant trunk moves. Continuum devices can, for example, be formed as nested, concentric, pre-curved elastic tubes ("concentric tube continuum device"), as tendon (e.g., control wire) actuated flexible tubes, as a series of axially arranged actuatable joints (such as the recently developed elephant trunk robots), or as a series of arms linked together via hinges or universal joints.

The snare tool(s) also can have a variety of configurations. The snare tool can be any member, flexible or rigid, operated manually or robotically, to deliver an end effector (e.g., snare device—snare loop, hook, grasper, etc.) to grasp and thereby support, position, maneuver, or otherwise control the flexible device. For example, the snare tool can be configured as a flexible or rigid tube or rod. A flexible snare tool can, for example, be flexible so as to permit navigation to the flexible device, and actuatable so as to become rigid in order to enable manipulation of the grasped flexible device. Like the flexible device, the snare tool can also be a continuum device having any of the characteristics described above in reference to the flexible device.

Figure 1:
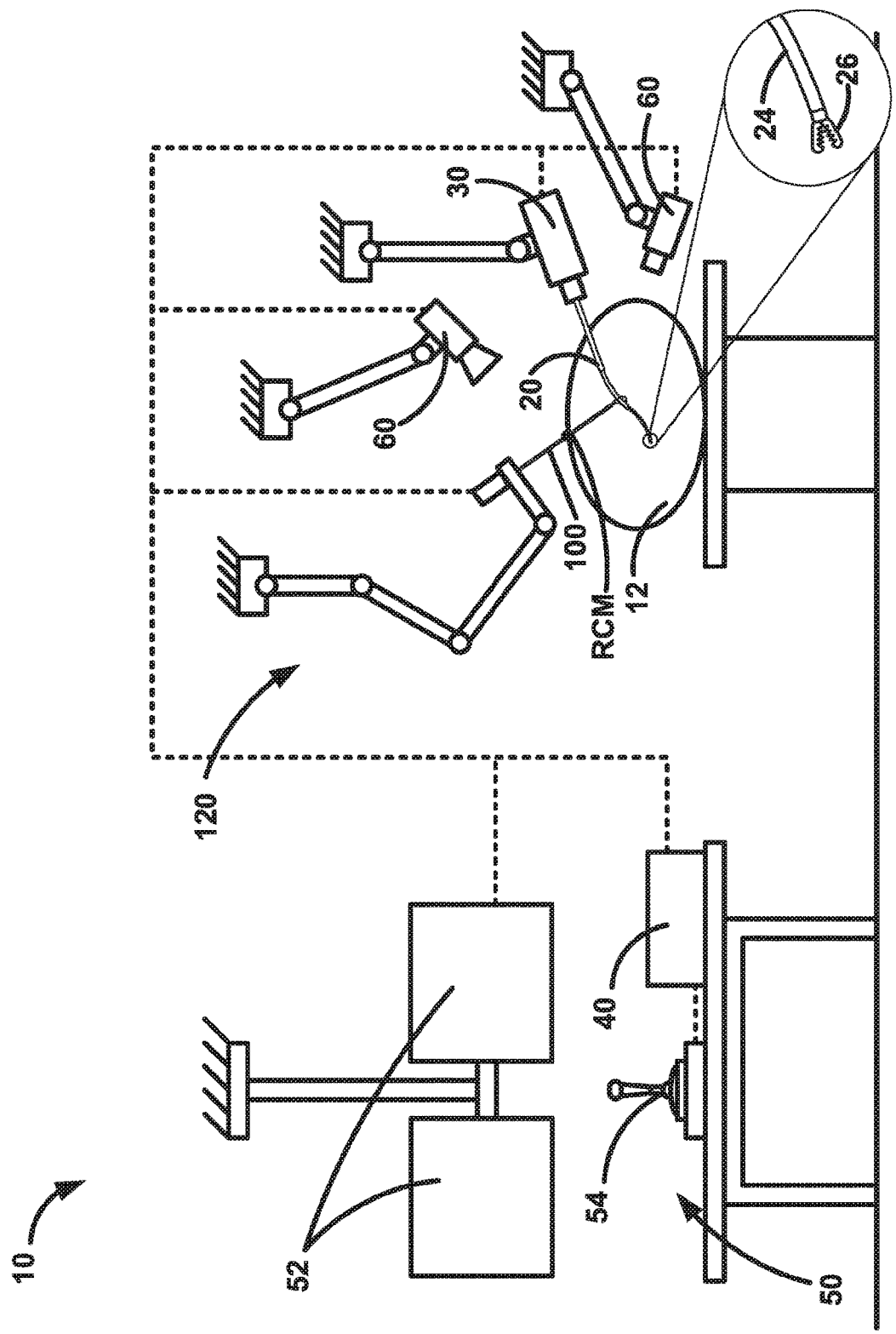
FIG. 1 illustrates an example configuration of a snare tool manipulator system.

Referring to FIG. 1, in this description, the snare tool manipulator system 10 is illustrated and described in a robotic surgery implementation in which the snare tool(s)

100 are used to manipulate a flexible device 20 in the form of a robotic continuum device. This description is illustrative of only one potential implementation of the snare tool manipulator system. The snare tool manipulator system is applicable to any implementation in which it may be desirable to use a flexible device and to supplement that use with the support, positioning, maneuvering, and control afforded through use of one or more snare tools. The following description of the snare tool manipulator system 10 is therefore by way of example only and is in no way meant to limit the scope of the claims appended hereto.

Referring to FIG. 1, the snare tool manipulator system 10 includes a flexible device 20 and one or more snare tools 100 for helping to manipulate the flexible device. In the example configuration of FIG. 1, the flexible device 20 is in the form of a robotically actuated continuum device for surgically delivering an end effector to a worksite 14 in a patient 12. The snare tool 100 is a robotically actuated rigid tubular device configured to deliver surgically in the patient 12 an end effector (e.g., a snare loop, hook, grasper, etc.) configured to snare or otherwise grasp the continuum device 20.

The tubes 22 of the continuum device 20 can be extremely small, needle-like tubes having diameters, for example, of less than 3.0 millimeters. The continuum device 20 can thus be inserted into the patient 12 in a minimally invasive manner. For example, the continuum device 20 can be inserted into the patient 12 through a very small incision or in an incisionless manner, i.e., via a puncture insertion. A tip 24 of the continuum device 20 carries one or more tools 26 for performing a surgical procedure. The continuum device 20 is operable robotically to cause translational and/or rotational movement of the tubes 22 relative to the patient 12 and to each other.

The tube(s) 22 of the continuum device 20 can, for example, be constructed of a superelastic material, such as a nickel-titanium alloy or "nitinol," and can have end portions that are pre-curved to a predetermined shape or curvature. An outermost one of the tubes can be a straight, rigid tube into which the inner tubes can be retracted, causing their respective curves to straighten and conform to the straight outer tube. As the inner tubes are extended out of the outer tube, they return to their pre-curved shape due to their superelastic properties.

The continuum device 20 can include an actuator 30 for actuating the tubes 22 in order to produce rotational and translational movement of the tubes. The actuator 30 can, for example, include electric motors that can be selectively operated to produce the desired tube movements. The motors can be connected to the tubes 22 directly or through a transmission element. As shown in FIG. 1, the actuator 30 can serve as the foundation or mount from which the continuum device 20 is supported relative to the patient 12. Additionally or alternatively, the continuum device 20 can be moved via gross movement of the device, e.g., by adjusting the position from outside the patient 12.

The system 10 includes one or more controllers, referred to herein generically as a controller 40, for controlling the operation of the various system components. The system 10 also includes a user interface 50, including a display 52 for viewing the procedure (e.g., via a robot mounted point-of-view "POV" camera) and haptic device 54, such as a joystick with pushbuttons or trigger actuators. The controller 40 can, for example, be a personal computer "PC" running software programmed to control operation of the continuum device 20 in response to inputs received from the user interface 50. In one example configuration, movement of the continuum device 20 can be effectuated through manipulation of the joystick and actuation of the tool 26 can be effectuated through actuation of the trigger/pushbuttons. To achieve this, the controller 40 can, for example, interface with components of the continuum device 20, such as motor controllers that operate the electric motors of the actuator 30, which drive the rotational and translational movement of the robot tubes.

Knowing the pre-curved configurations of the tubes of the continuum device 20, the controller 40 can be programmed with a kinematic model of the robot. The controller 40 can use this model as a map for determining how to actuate the continuum device 20, i.e., how to translate and rotate the tubes 22, in response to inputs received from the user interface 40 in order to achieve the desired movement of the tip 24. The system 10 can include one or more sensing devices 60, such as video, CT scan, x-ray, ultrasound, MRI, etc., that provide continuum device 20 position data for informing the controller 40 and the user (via the display 52) of actual robot and/or tool positions. The tubes 22 can be outfitted with markers, e.g., radio-opaque markers, for helping to identify the robot and/or tool position. The controller 40 can take actual robot position data into account when calculating responses to inputs from the user interface 50.

The system 10 also includes one or more snare tools 100 for helping to maneuver or otherwise actuate or control the continuum device 20. Referring to FIGS. 2 and 3A-3D, the snare tool 100 includes a shaft 102 and a snare 104 that extends from a tip 106 of the shaft. The shaft 102 can be solid (one or more rods) or tubular (one or more tubes) in form, can be rigid or flexible in form, and can have a single or multiple component construction. The snare tube 102 can be straight or they can be curved with a preset or variable shape. As such, the shaft 102 can be constructed of a material or materials that promote these structural qualities.

In one example configuration, a rigid shaft 102 can be formed of surgical stainless steel, and a flexible shaft could be formed out of a nickel-titanium "nitinol" alloy. As another example configuration, a multiple component shaft 102 can be tubular in form and include multiple tubes arranged in a concentric and telescoping manner. In fact, in this instance, the shaft 102 can take the form of a continuum device including nested sets of pre-curved elastic segments that bend themselves and each other when translated or rotated. The nested sets of pre-curved needles could be actuated automatically, or manipulated by hand and then locked in place. As yet another example configuration, the snare tube 102 can have a variable shape that is actuated via wires or tendons. The rigidity or stiffness of the snare tube 102 can also vary, for example, via flexure hinges. As a further example configuration, a multiple component shaft 102 can include solid or tubular shaft segments interconnected via hinges.

Like the continuum device tubes 22, the shaft 102 can have a small, needle sized diameter, e.g., less than 3.0 millimeters, and therefore can be capable of being introduced into the patient percutaneously through either a small incision or puncture insertion. In tubular constructions, the shaft 102 includes an inner channel through which the snare 104 can extend.

FIGS. 3A-3D illustrate generally the process for using the snare tool manipulator system 10. Referring to FIGS. 3A-3D, in use, the shaft 102 of the snare tool 100 is inserted percutaneously to position the tip 106 at a desired location in the patient 12. This is indicated generally by the arrow in FIG. 3A. Note that, during insertion and initial positioning of the shaft 102, the snare 104 is retracted into the shaft. Referring to FIG. 3B, when the snare tool 100 is inserted such that the tip 106 is positioned in the desired location, the snare 104 is expanded, as indicated generally by the arrows in FIG. 3B. This can be done, for example, by extending or "pushing" the snare wire 108 distally from the snare tube 102.

Referring to FIG. 3C, the flexible device 20, e.g., the continuum device, is extended through the open snare 104, as indicated generally by the arrow in FIG. 3C. When the flexible device 20 is positioned at the desired within the snare 104, the snare can be closed to tighten onto and grasp the flexible device 20. The flexible device 20 can then be manipulated through operation of the snare tool 100, as described herein.

The snare 104 can have a variety of constructions. For example, the snare 104 can be constructed of a solid, twisted, or braided metal (e.g., stainless steel) wire. Other biocompatible materials, such as silk, nylon, and various plastics/polymers can also be used.

The snare tool 100 is configured to be inserted into the patient 12 and maneuvered to capture or snare the continuum device 20. In the embodiment illustrated in FIGS. 1-3, the snare 104 includes a noose or loop 108 constructed of stainless steel cable or wire. The snare loop 108 can be actuated open (i.e., enlarged in diameter) by pushing or extending the snare cable/wire through the snare tube 102, or closed (i.e., reduced in diameter) by pulling or retracting the snare cable/wire into the snare tube 102. In this configuration, the snare tool 100 can be inserted into the patient 12 and the snare loop 108 can be opened in order to receive the continuum device 20. Once the tip 24 of the continuum device 20 has passed through the snare loop 108 and the robot achieves a desired position within the patient 12, the loop can be tightened to secure the snared robot tube 22 to the tip 106 of the snare shaft 104.

Those skilled in the art will appreciate that the snare 104 can be configured in a variety of manners to form the snare loop 108 within the snare shaft 102. For example, the cable/wire forming the snare 104 can be doubled over and passed through the shaft 102 with the closed, doubled-over end positioned distally in the tube. The snare loop 108 can be that portion of the doubled-over distal end of the cable/wire that protrudes from the tip 106 of the shaft 104. In this example configuration, the snare loop can be actuated by extending/retracting both legs of the doubled over cable/wire in the snare tube 102.

Alternatively, one end of the doubled-over cable/wire can be anchored to the snare 100, e.g., to the snare tube 102, and doubled over in the tube with the doubled over end positioned distally therein. In this example configuration, the snare loop 108 can be actuated by extending/retracting the non-anchored leg of the doubled over cable/wire in the snare tube 102.

As another alternative, the snare 104 can have a hooked configuration instead of a looped configuration. In this example configuration, the snare 104 could be formed of a material having a more rigid construction, such as stainless steel wire. Alternatively, the snare could be constructed as a separate piece, e.g., of stamped or die-formed stainless steel, that is secured to the cable/wire. The hook could be extended out of the snare tube 102 and retracted into the snare tube in order to grasp the continuum device 20. Advantageously, a hooked configuration of the snare 104 would allow for grasping the tubes 22 even after the robot tip 24 has passed by. Other alternatives, such as clamping mechanisms or graspers would also provide this functionality.

The system 10 includes an actuation unit 120 for actuating the snare tool 100 and controlling its position in space. The actuation unit 120 can take several forms. For example, the actuation unit 120 can include multiple revolute links configured to maneuver the snare tools 100 around a remote center-of-motion (RCM). The actuation unit 120 can be specifically designed to mechanically enforce an RCM, or it can be controlled in a way that virtually enforces the RCM. The RCM can be programmed to move in time rather than being static, e.g., to move with the patient's body when the patient 12 breaths. In the context of minimally invasive procedures performed by the system 10, the RCM is the point where the snare tool enters the patient, which is illustrated in FIG. 1.

Figure 2:
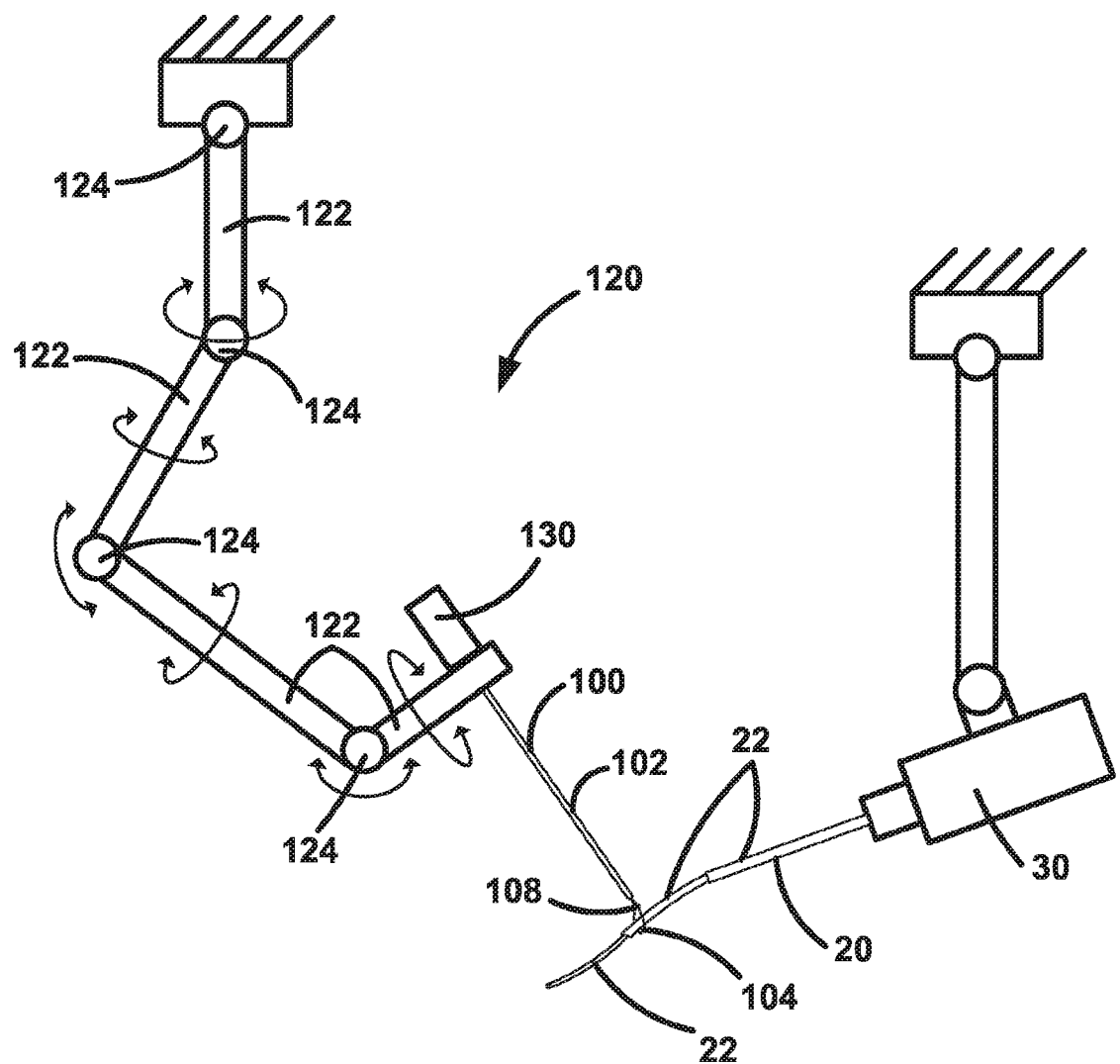
FIG. 2 is a magnified view of a portion of the system of FIG. 1.
Figure 7B:
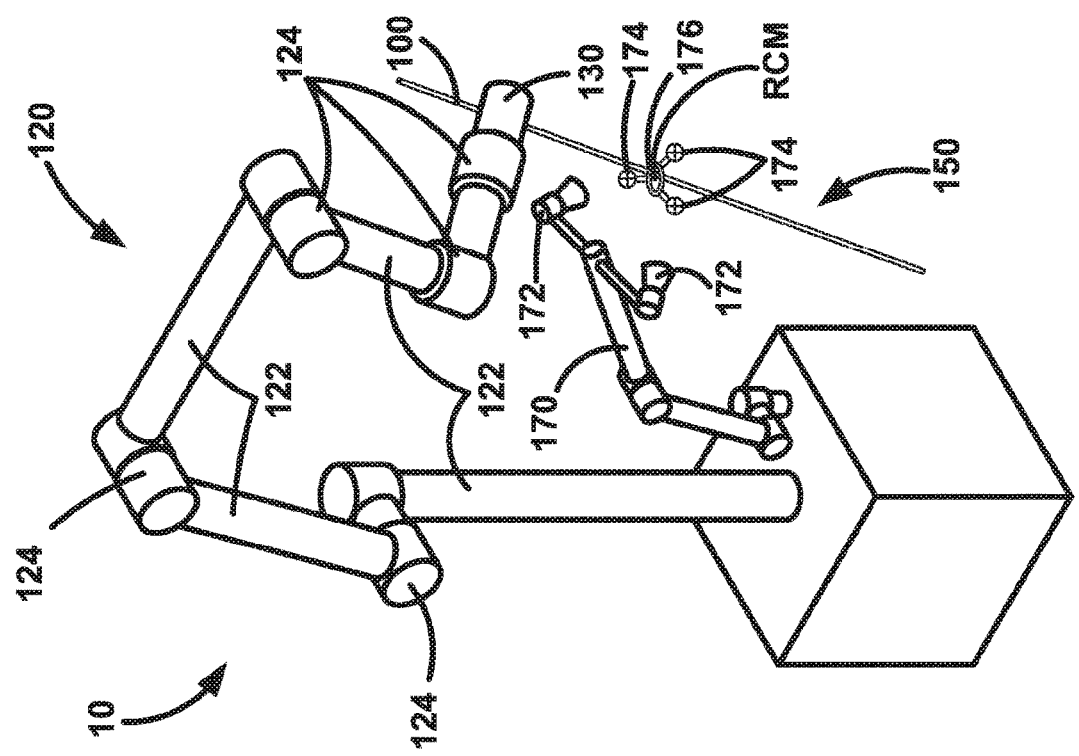
FIGS. 7A and 7B illustrate different tracking configurations of the system of FIGS. 1-3.
Figure 7A:
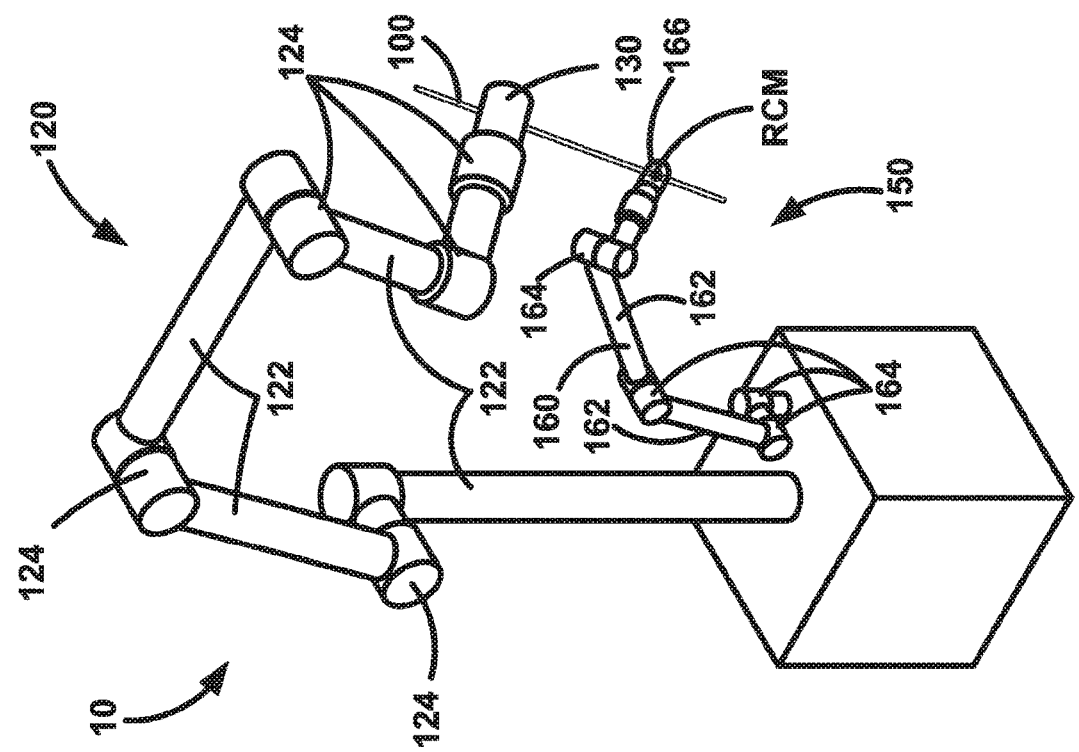

In an example configuration, the actuation unit 120 can take the form of a robotic arm, which is illustrated schematically in FIGS. 1, 2, and 7A-7B. Referring to FIG. 2, 7A-7B, the robotic arm 120 includes a plurality of arm segments 122 that are connected to each other by joints 124. Each joint 124 can facilitate pivotal relative movement between the adjacent pairs of arms 122 to which it is connected. The joints 124 can also permit rotation of the distally connected arm 122 of its connected pair about a longitudinal axis of the arm. This pivotal and rotational movement of the arms 122 is indicated generally by double-ended arrows in FIG. 2.

The snare tool 100 is supported at the distal end of the robotic arm 120 by a snare actuator 130. The snare actuator 130 actuates the snare loop 108, for example, through extension/retraction of the snare cable/wire as described above. In certain configurations, the snare actuator 130 can also provide rotation and translation of the snare tool 100, as indicated generally by double-ended arrows in FIG. 2. Through the operation of the robotic arm 120 and snare actuator 130, the snare tool 100 can be maneuvered in space while enforcing the RCM.

The actuation unit 120 can be automated and controlled by a computer, e.g., the controller 40, that accepts input from the operator (e.g., via the user interface 50), or it can be a mechanical system that is manually operated. The actuation unit 120 can also be designed to act as a static fixture that doesn't move at all. In this case, the actuation unit 120 can be designed to be mechanically passive (i.e., the operator can easily position it manually) with a brake system that locks it in place once positioned in the desired configuration.

The actuation unit 120 can include sensing elements that detect its configuration. For example, each joint 124 of the robotic arm 120 can include an angular position sensor that provides an angular position signal relative to a home position. With this information and knowing the length of each arm, the controller 40 can determine the position of the snare actuator 130. Additionally, the snare actuator 130 can know the position of the snare tool 100, particularly the tip of the snare tube 102 and the snare loop 108. Armed with this positional data, the controller 40 can know the position and orientation of the snare tool 100 at all times. The controller 40 can processes this information and use it to determine how to control the actuation unit 120 and snare actuator. The information can also be displayed to the operator via the display 52 and recorded on a storage medium in the controller 40.

The actuation unit 120 can be rigidly mounted, e.g., to a bed, floor, or ceiling, or it can be mounted to a wheeled base that can be moved around the surgical suite by hand. The wheeled base can incorporate one or more actuation units for actuating multiple snare tools or other robotically actuated instruments. In this instance, the controller 50 can include collision avoidance programming to ensure the actuation units do not collide with one another. Alternatively, the actuation units can have a mechanical configuration or design that ensures they remain collision-free. The actuation unit 120 can even be patient-mounted.

It can be important for the controller 40 to maintain the remote center-of-motion (RCM) of the snare tool 100, especially in the surgical implementation in which the RCM is located at the entry point of the patient. To assist in this, the system 10 can include a measurement system 150 for providing RCM tracking information to the controller 40. The controller 40 can use the RCM tracking information to track the entry point of the snare tool 100, which can change during the procedure. For example, if the snare tool 100 is inserted between a patient's ribs and the patient breathes, the entry point and the RCM will move. The controller 40, receiving the RCM and entry point location data, can adjust the position and/or orientation of the snare tool 100 accordingly to maintain the RCM at the entry point.

FIGS. 7A and 7B illustrate two different measurement systems 150 for tracking the entry point and RCM of the snare tool 100. Referring to FIG. 7A, the measurement system 150 is a mechanical system including an articulated arm 160 with arm sections 162 linked by joints 164 that provide free movement in all directions. An RCM connector 166 positioned at the end of the arm 160 is connected mechanically to the snare tool 100 at the RCM and moves with the snare tool when actuated by the robotic arm 120. Sensors in the arm 160 (e.g., rotational position sensors in the joints 164) detect movement of the RCM and provide indication of the same to the controller 40.

Referring to FIG. 7B, the measurement system 150 can be an optical tracking system that visually tracks the entry point. In this instance, the measurement system 150 can include cameras 172 that are mounted to a positioning arm 170. The cameras 172 track the RCM by tracking one or more fiducial targets 174 that register with the cameras 170. The fiducial targets 172 can, for example, be mounted on a fiducial frame 176 that is secured to the patient (e.g., via tape) and through which the snare tool 100 passes.

Figure 4A:
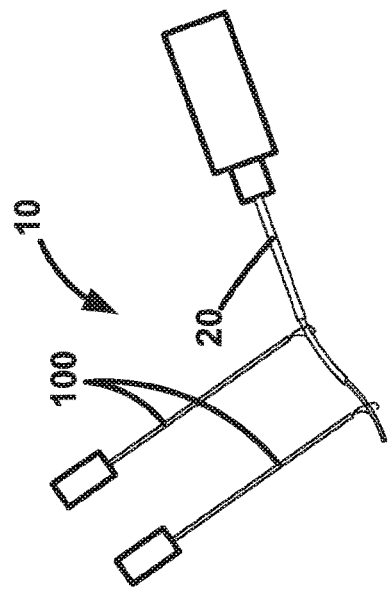

In FIGS. 1-3, the system 10 is illustrated as implementing a single snare tool 100 for helping to manipulate the continuum device 20. The system 10 could, however, include multiple snare tools 100 working in concert to help manipulate the continuum device 20. Examples of multiple snare tool 100 configurations that can be implemented in the system 10 are illustrated in FIGS. 4A-4J. FIG. 4A illustrates the configuration of the system 10 illustrated in FIGS. 1-3, in which a single snare tool 100 is used to snare and help control the continuum device 20.

Figure 4B:
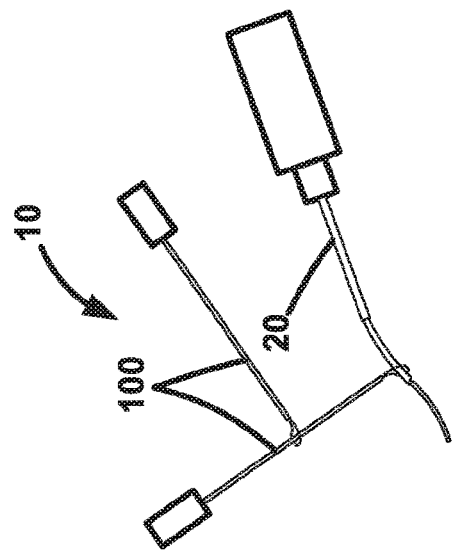

FIG. 4B illustrates a configuration of the system 10 in which two snare tools 100 are used to snare and help control the continuum device 20 in parallel. This configuration provides the added strength and stability of a parallel robotic actuator structure.

Figure 4C:
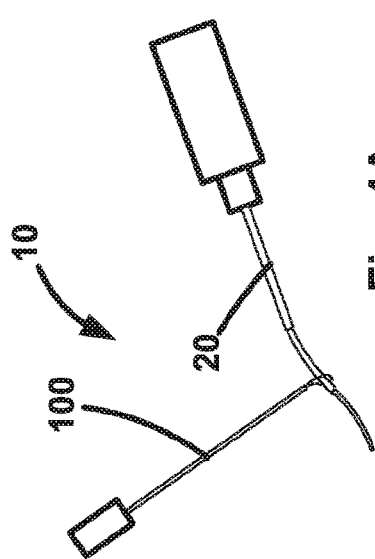

FIG. 4C illustrates a configuration of the system 10 in which two snare tools 100 are used to snare the continuum device 20 at the same location but from different angles. This configuration can help provide added strength and stability at the snare location.

Figure 4D:
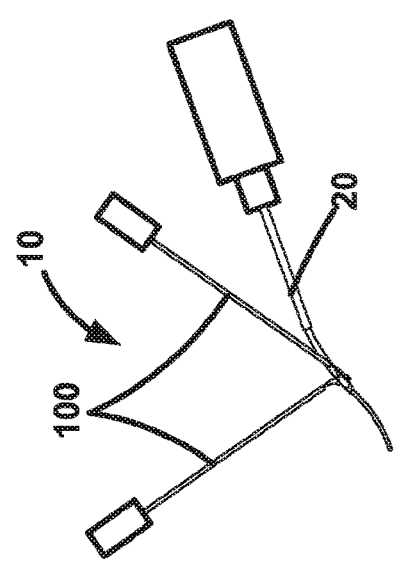

FIG. 4D illustrates a configuration of the system 10 in which two snare tools 100 are used to help control the continuum device 20. In this configuration, a first snare tool 100 snares the continuum device 20 and a second snare tool snares the first snare tool. In this configuration, the second snare tool 100 can help provide added lateral strength and stability to the first snare tool.

FIG. 4E illustrates a configuration of the system 10 in which three snare tools 100 are used to snare and help control the continuum device 20 in parallel. This configuration provides the additional strength and stability, even greater than that of the parallel robotic actuator structure of FIG. 4B.

FIG. 4F illustrates a configuration of the system 10 in which three snare tools 100 are used to snare and help control the continuum device 20. This configuration combines the features of the systems of FIGS. 4B and 4D. Two of the snare tools 100 snare the continuum device 20 in parallel and provide the added strength and stability of a parallel robotic actuator structure. a third snare tool 100 snares one of the other first snare tools and thus can help provide added lateral strength and stability to the first snare tool.

FIG. 4G illustrates a configuration of the system 10 in which three snare tools 100 are used to help control the continuum device 20. In this configuration, a first snare tool 100 snares the continuum device 20. Second and third snare tools 100 snare the first snare tool at different locations and from opposite directions. In this configuration, the second and third snare tools 100 can help provide added lateral strength and stability to the first snare tool, even greater than that added by the single snare tool of FIG. 4D.

FIG. 4H illustrates a configuration of the system 10 in which three snare tools 100 are used to help control the continuum device 20. In this configuration, a first snare tool 100 snares the continuum device 20. A second snare tool 100 snares the first snare tool from a generally perpendicular direction. A third snare tool 100 snares the second snare tool from a generally perpendicular direction. In this configuration, the second and third snare tools 100 can help provide added lateral strength and stability to the first snare tool, even greater than that added by the single snare tool of FIG. 4D.

Figure 4I:
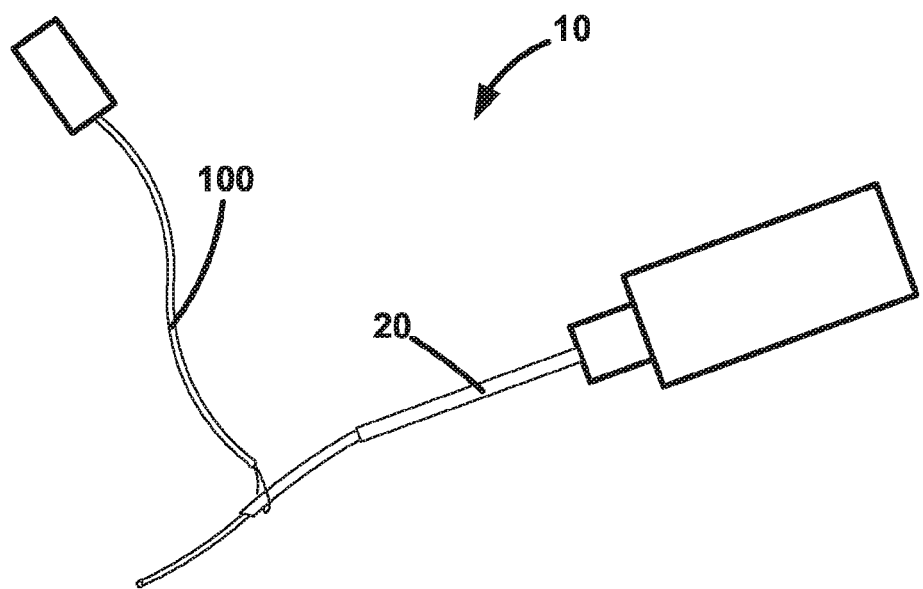

FIG. 4I illustrates a configuration of the system 10 in which a single snare tool 100 is used to help control the continuum device 20. In this configuration, the snare tool 100, instead of having a straight configuration like those of FIGS. 4A-4H, has a curved configuration. The curved configuration can be obtained, for example, by bending or otherwise pre-forming the snare tool 100 to a predetermined shape. The snare tool 100 can, for example, have a material construction selected so that it can be bent to the predetermined shape, yet remain rigid enough to exert the forces necessary during use without deflection/deformation. Alternatively, the snare tool 100 can have a jointed or hinged construction that permits the shape to be selected and then locked mechanically.

Figure 4J:
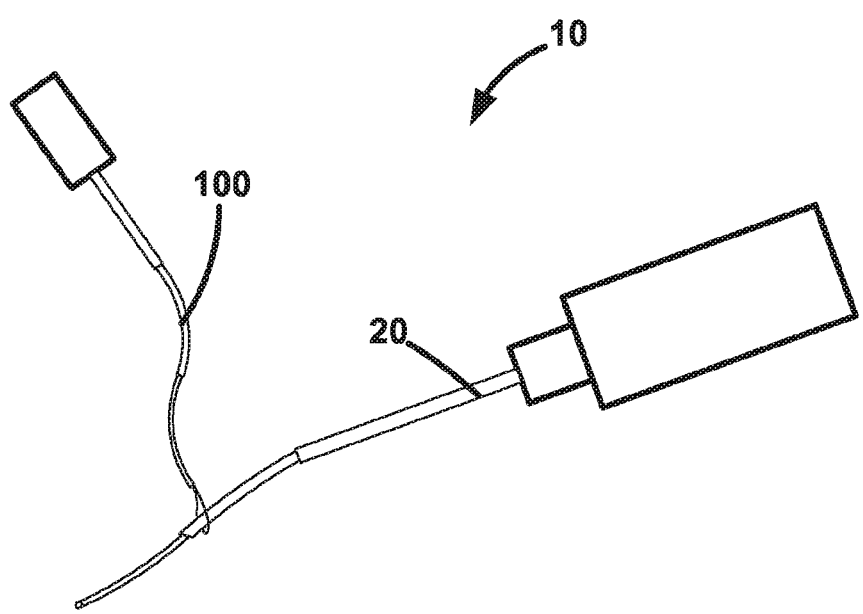

FIG. 4J illustrates a configuration of the system 10 in which a single snare tool 100 is used to help control the continuum device 20. In this configuration, the snare tool 100 is provided in the form of a continuum device having a nested, concentric, precurved tube configuration similar to that of the continuum device 20. In this configuration, the snare tool 100 can be configured and reconfigured as needed. Additionally, the snare tool 100 can be maneuvered through actuation of the actuator arm 120 (see, e.g., FIGS. 1 and 2), through actuation of the continuum device, or a combination thereof.

In the example configurations of FIGS. 4B-4H, the multiple snare tools 100 are illustrated as being arranged with their respective tube axes extending in a generally coplanar manner. The snare tools 100 could, however, be arranged with their tube axes extending along different planes. This can be the case, for example, where stability is desired along multiple planes or directions. Also, FIGS. 4A-4J are no way meant to limit the system 10 to these example configurations. FIGS. 4A-4J are merely examples of possible implementations of the snare tools 100 meant to illustrate the fact that the possible configurations are virtually limitless. For example, any of the straight and curved tube configurations of the snare tools 100 illustrated in FIGS. 4A-4J can be used in combination with each other.

Furthermore, the example configurations of the system 10 illustrated in FIGS. 4A-4J are not meant to limit the snare tools 100 to use with the continuum device 20. Rather, the snare tools 100 can be used to manipulate and control any rigid or flexible device 20, whether robotic or manually operated. For example, the flexible device 20 can be an active flexible device such as one that deflects when a tendon is pulled (e.g., flexible endoscope), which is controlled with a motorized actuation unit (robotic) or operated manually. The flexible device 20 could have a working channel, down which an additional tool can be deployed. The flexible device 20 can also contain a visualization element such as optical fibers or a camera. The flexible device 20 can be passive in the sense that the snare tools 100 are the sole means to actuation. Examples of passive flexible devices 20 for which the snare tools 100 are the sole means of actuation include a long, flexible gripper, an irrigation tube, a vacuum tube, or an ablation device.

Multiple types of flexible devices 20 can be used simultaneously and several flexible devices can be grasped at the same time by a single snare tool 100. An example of using multiple flexible devices could be two flexible endoscopes that are manipulated near one another. In this case, the camera views from both endoscopes could be stitched together to create a stereo view. In another example, a flexible endoscope could be manipulated at the same time as a long flexible gripper. In this case, the endoscope could be maneuvered to maintain a clear view of the gripper for resection tasks.

In another example configuration, the flexible device 20 can be an un-tethered module that is maneuvered inside the body by the snare tools 100. In this case, the un-tethered module 20 could be a surgical stapler module, an ultrasound probe, a tactile array, or a camera. The module 20 may be attached to a tether or it may be un-tethered, such as in the case of a wireless capsule endoscope.

Figure 5A:
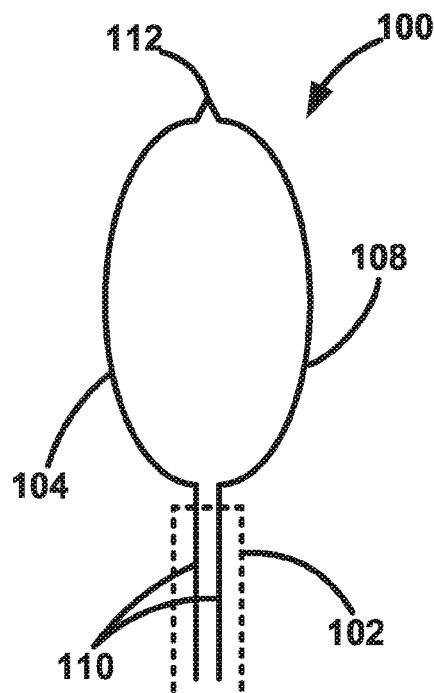
FIGS. 5A-5D illustrate different example snare loop configurations that can be implemented in the system of FIGS. 1-3.
Figure 5B:
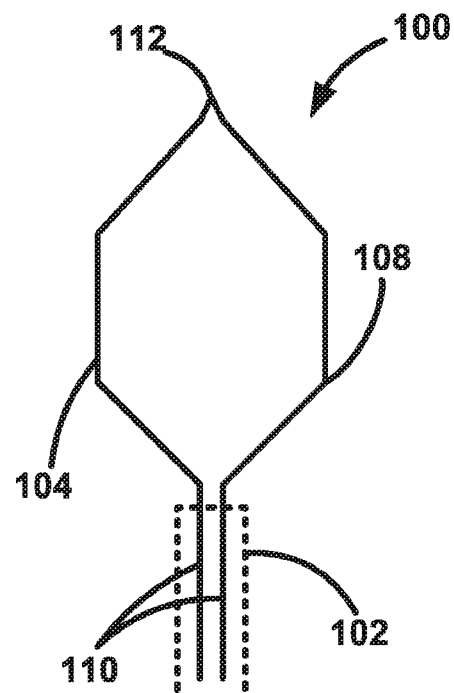
Figure 5C:
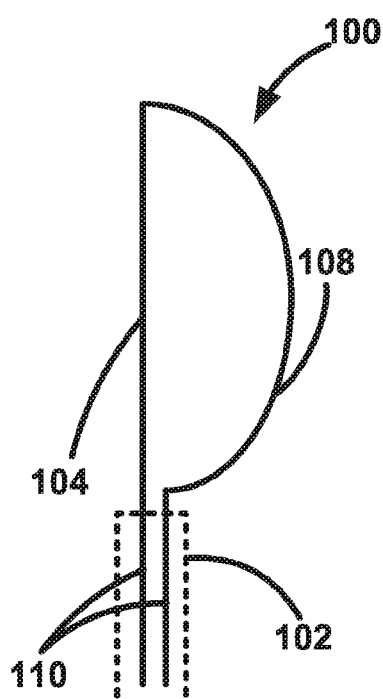
Figure 5D:
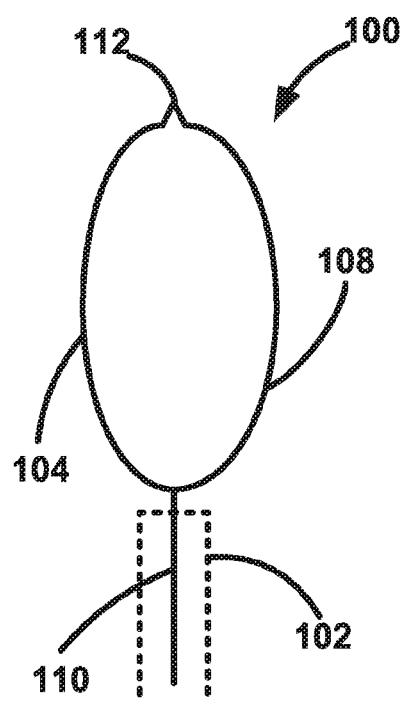

The snare loop 108 can be configured to take on a specific shape when deployed through the snare tube 102. FIGS. 5A-5D illustrate some example configurations of the snare loop 108. In FIG. 5A, the snare wire 104 includes two wire leads 110 that extend through the snare tube 102 and a snare loop 108 that has a generally rounded, oblong or oval shape. In FIG. 5B, the snare wire 104 includes two wire leads 110 that extend through the snare tube 102 and a snare loop 108 that has a generally hexagonal shape. In FIG. 5C, the snare wire 104 includes two wire leads 110 that extend through the snare tube 102 and a snare loop 108 that has a generally D-shaped configuration with one straight wire leg and one curved wire leg. In FIG. 5D, the snare wire 104 includes a single wire lead 110 that extends through the snare tube 102 and a snare loop 108 that has a generally rounded, oblong or oval shape. In the example configurations of FIGS. 5A, 5B, and 5D, the snare loop 108 includes a terminal pointed portion 112, the purpose of which is to help guide the snare wire 104 through the snare tube 102 without getting caught or binding-up.

The snare wire 104 can be pulled tight robotically by the snare actuator 130 or by hand in an manually operated configuration. Depending on the configuration, the snare loop 108 can also be locked in the tensioned/snared condition either manually or automatically.

The snare tools 100 can include sensing elements that detect some or all of the snare tool components. The information obtained from the sensor can be sent to the controller 40, which can process and use the information to govern how the system behaves. The information can also be displayed to the operator via the display 52. The information can be recorded on a storage medium in the controller 40 for subsequent analysis.

The snare tools 100 can include a mounting module that is used to attach it to the snare actuator 130 and/or the robotic arm 120. This mounting module can have a quick release mechanism that rapidly disconnects the snare tools 100 from the snare actuator 130 and/or the robotic arm. The quick release mechanism can be triggered remotely by a signal from the operator, it can be triggered by a button or lever attached to the snare tool 100, snare actuator 130, or robotic arm 120. The release mechanism can be configured to release automatically on the command of the controller if certain conditions are detected.

Aside from manipulating the flexible devices 20 inside the patient 12, the snare tools 100 can also be used to power devices inside the patient. For example, Referring to FIG. 6A, the snare tool 100 can deliver power to a device inside the patient 12 through a twisting/rotating motion. In this configuration, the snare tool can be configured to have a simple mechanical engagement or linkage feature that interlocks with the device inside the patient 12 so that the rotational force can be transferred from the snare tool 100 to the surgical tool on the flexible device 20. In the example configuration of FIG. 6A, this mechanical engagement feature takes the form of a flat-head screwdriver for being received in a slot in the corresponding portion of the tool mounted on the flexible device 20. In FIG. 6B, rotation is imparted to the snare wire 104 individually or to the snare tube 102 to rotate both the snare tube and the wire so that the snare loop 108 and the tool on the flexible device 20 to which it is snared rotates along.

Figure 6C:
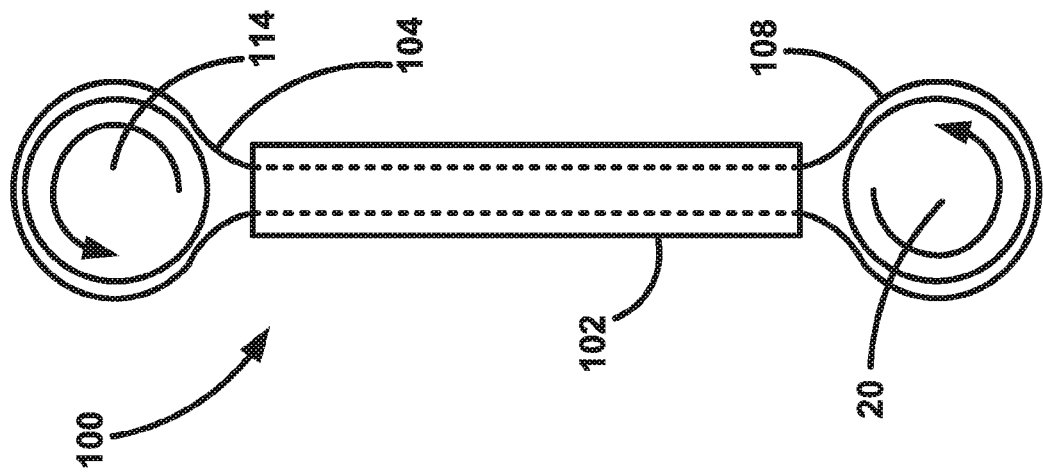
FIGS. 6A-6C illustrate different example working implementations configurations of a snare tool that can be implemented in the system of FIGS. 1-3.
Figure 6B:
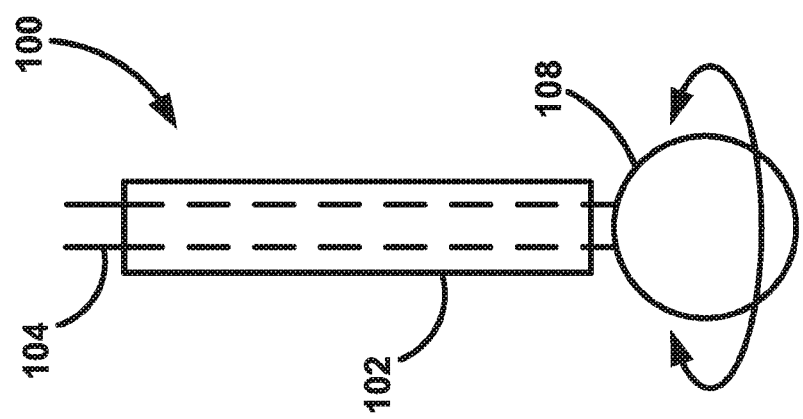
Figure 6A:
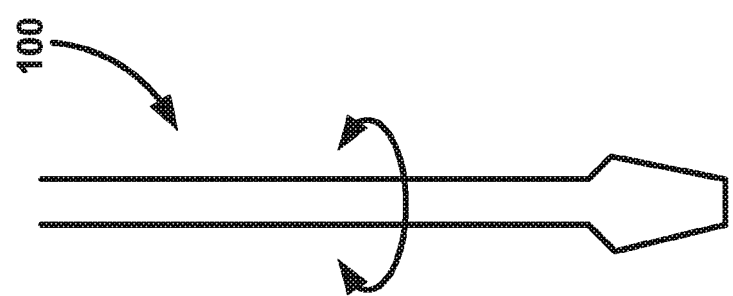

In FIG. 6C, the snare wire 104 is formed in an endless loop and is driven in the manner of a belt by a drive element 114 externally of the patient 12. The rotational force imparted to the snare wire 104 causes it to act as a belt drive and rotate the tool on the flexible device 20 around which the snare loop 108 extends. As a further alternative, the snare tool 100 could be used to deliver electrical energy to a tool located on the flexible device 20 in the patient.

The snare tool 100 can be configured so that the snare wire 104 is removable easily while the snare tube 102 remains positioned in the patient 12. This can allow the hollow snare tube 102 to be used like an ordinary needle, for example, to deliver fluids, medication, radioactive seeds, etc. The snare wire 104 can also be replaced with any type of tool that can fit within the inner diameter of the snare tube 102. The snare tube 102 can also be used as a simple probe. The snare wire 104 can be designed in a way that makes it useful to both grab the flexible device 20 inside the patient 12 and also to manipulate tissue, e.g., by grasping the tissue or using the snare tool 100 as a retractor.

System Control

Control of the system 10, particularly the snare tools 100, presents somewhat unique aspects. Because the snare tools 100 are inserted into the patient 12 either through small incisions or through puncture insertion, care must be exercised while manipulating the snare tool from outside the patient. This is because the position of the portion of the snare tool that extends through the incision/puncture opening (indicated generally at 16 in FIG. 8) must be maintained. This is referred to herein as maintaining a remote center of motion ("RCM").

Figure 8:
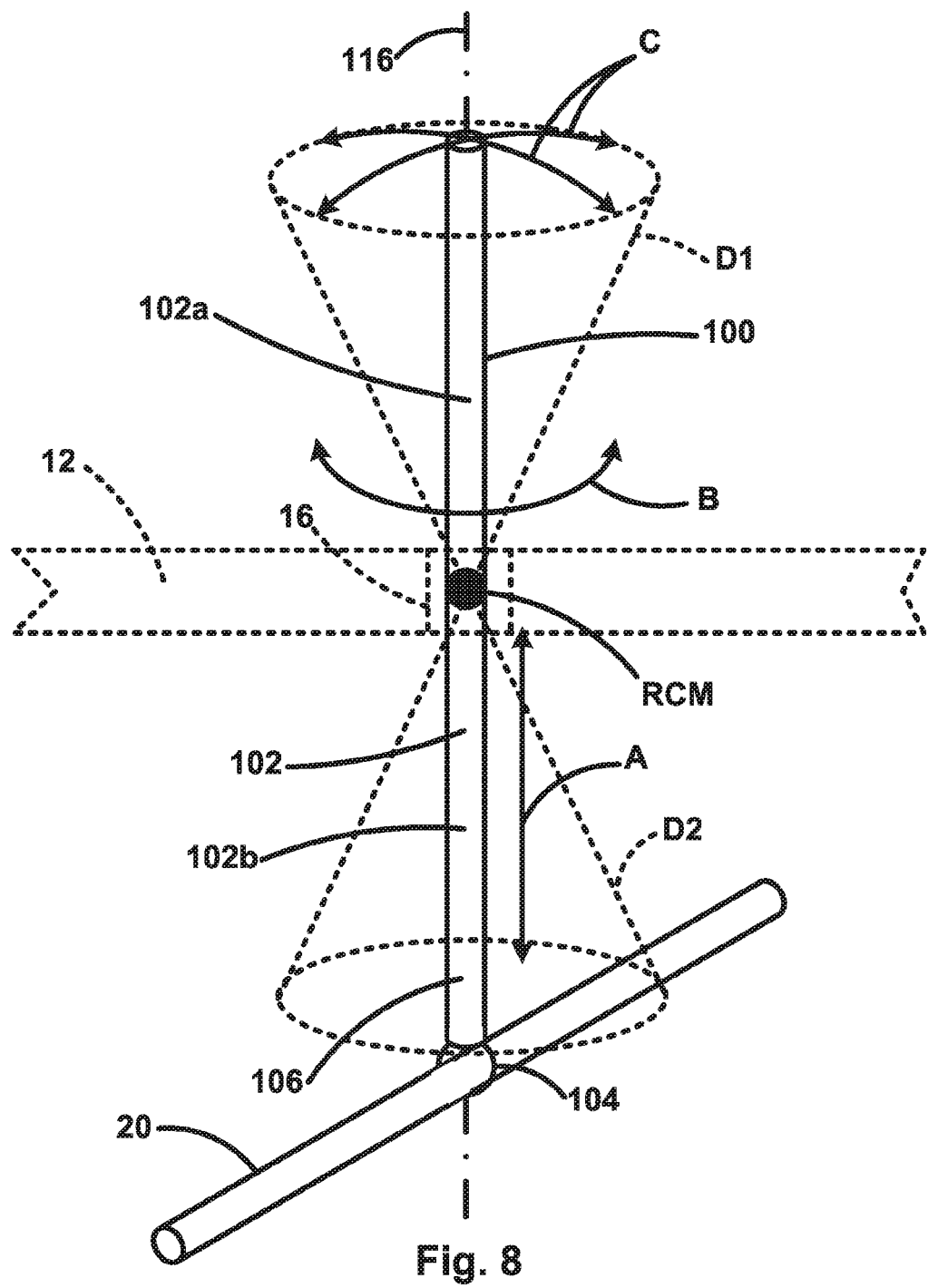
FIG. 8 illustrates control aspects related to the operation of the system.

Referring to FIG. 8, when the snare tool 100 is inserted percutaneously into the patient 12, the RCM is positioned at the point of insertion. The snare tool 100 secures the flexible device 20 via the snare 104 (as described above in reference to FIGS. 3A-3D) and can manipulate the flexible device, for example, through operation of the actuation unit 120 (see, e.g., FIGS. 1, 2, 7A-B). In doing so, the snare tool 100 enjoys several degrees of freedom.

The snare tool 100 has an axial degree of freedom, indicated generally by the arrow labeled A in FIG. 8. In this axial degree of freedom, the snare tool 100 can be moved axially into and out of the patient 12 through the opening 16 along a central axis 116 of the snare tool. Movement of the snare tool 100 in the axial degree of freedom should not affect maintaining the RCM, as long as the RCM was maintained prior to the axial movement.

The snare tool 100 also has a rotational degree of freedom, indicated generally by the arrow labeled B in FIG. 8. In this rotational degree of freedom, the snare tool 100 can be rotated about the axis 116. Movement of the snare tool 100 in the rotational degree of freedom also should not affect maintaining the RCM, as long as the RCM was maintained prior to the rotational movement.

Finally, the snare tool 100 has a pivotal degree of freedom, indicated generally by the crossed arrows labeled C and inverted cones labeled D1, D2 in FIG. 8. In this pivotal degree of freedom, the attitude of the snare tool 100 can be adjusted so that the orientation of the snare tool axis 116 changes. In doing so, the position of the tip 106 of the snare tool 100 within the patient 12 is adjusted. It is with this pivotal degree of freedom that maintenance of the RCM is important.

As can be seen from FIG. 8, the RCM divides the shaft 102 of the snare tool 100 into a portion 102a positioned outside the patient 12 and a portion 102b positioned inside the patient. The cones D1, D2 indicate the range of motion of the snare tool 100. In other words, the segment 102a outside the patient 12 can be moved to any position outside within its associated cone D1 to move the segment 102b inside the patient to a corresponding and opposite position within its associated cone D2. The size of the cones D1, D2 illustrated in FIG. 8 are by way of example only and are not meant to limit or otherwise define the range of motion for the snare tool 100. The range of motion could be greater than or less than that illustrated in FIG. 8.

From this, it can be seen that maintaining the RCM of the snare tool 100 equates to maintaining the opposing tips of the cones D1, D2 at that same location throughout the procedure implementing the system 10 of FIG. 1. To do this, the system 100 (e.g., the controller 40) implements a control algorithm in which the controller receives the desired motion input from the user via the user interface 50 and produces snare tool motion via the actuation unit 120, all the while maintaining the RCM.

According to one aspect, the system 10 can implement a model-based Jacobian matrix to compute the necessary motion of the actuation unit 120 in order to achieve the desired motion of the snare tool 100. If the system 10 determines that the desired motion isn't possible in with the current configuration of snares, it can iteratively search for a more suitable configuration that accomplishes the user's needs.

Figure 9:
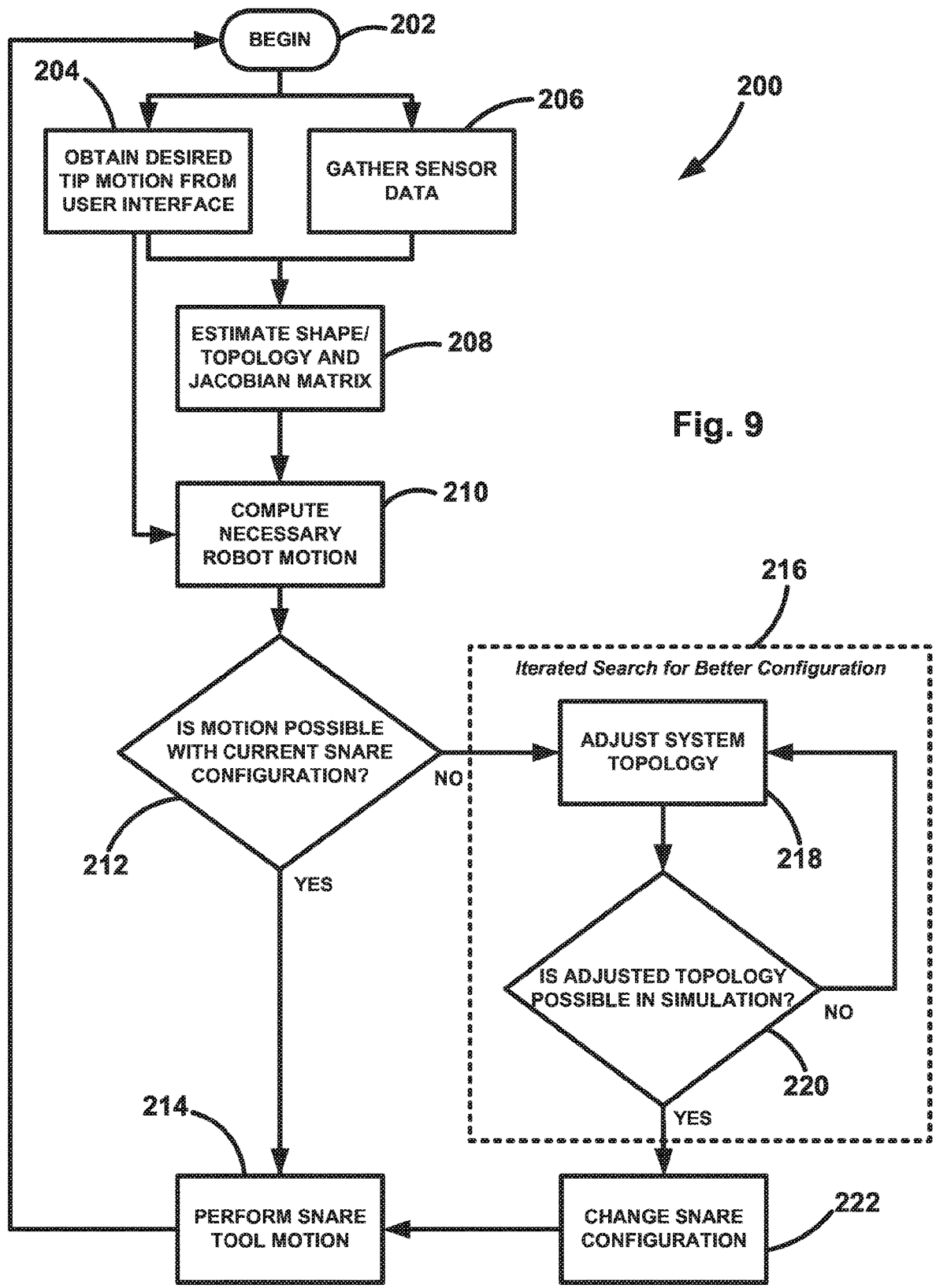
FIG. 9 is a flow diagram illustrating a control algorithm for the system.

A top-level diagram illustrating a process or algorithm 200 that can be implemented by the controller 40 to achieve this control is shown in FIG. 9. The order in which the steps of the following description of the process 200 is written is not intended to limit the process in any way. The steps described herein can be performed in any order and can be repeated without limitation. Certain steps may be skipped and certain steps can be executed a greater or lesser number of times than others.

Referring to FIG. 9, the process 200 begins at step 202 and proceeds to steps 204 and 206, where the desired tip motion is obtained from the user and sensor data regarding current conditions of the snare tool (e.g., tool position) is gathered from the system 10. This data is passed along to step 208, where the shape/topology of the current snare tool configuration and the Jacobian matrix for the tip motion requested by the user are estimated. These estimations are passed to step 210, where the necessary robot motion, i.e., the motion of the actuation unit 120 that will produce the desired tip motion, is computed. As shown in FIG. 8, this calculation may also require the desired tip motion information from step 204.

The computed robot motion determined at step 210 is passed to step 212, where a determination is made as to whether the computed robot motion is possible with the current configuration of the snare tool 100. If the computed motion is possible, the process 200 proceeds to step 214, where the snare tool motion is executed. The process 200 iterates back to the beginning at step 200 and repeats.

If, at step 212, it is determined that the motion computed at step 210 is not possible with the current configuration of the snare tool 100, the process 200 executes an iterated search, indicated generally at 216, for a better snare tool configuration. According to the iterated search 216, the process 200 proceeds to step 218, where the re-configuration or adjustment of the system topology is considered. By "topology" of the system, it is meant to describe the routes along which the continuum device 20 and snare tools 100 extend and the points at which the continuum device and snare tools are connected. FIGS. 4A-4J thus illustrated various example topologies of the system.

In adjusting the system topology at step 216, several system characteristics are considered. For example, the system can consider adjustments to: the number of snare tools implemented in the system, the position of each snare tool, and the angle or attitude with which the snare tool approaches the continuum device 20, and the shape of any curved or otherwise shape-adjustable snare tools, if applicable. The system can also contemplate adjusting the shape or configuration of the continuum device 20.

At step 216, in each iteration, the system can calculate or otherwise determine a model for the newly determined system topology for the current iteration. This topographic model can be mapped against and compared to a model of the workspace determined, for example, via medical imaging (MRI, CAT, PET, ultrasound, etc.). Using a simulation approach, the system determines via simulation, at step 218, whether the adjusted topology of the current iteration is possible. In doing so, the system determines whether the adjusted topology is feasible within the modeled workspace, and can take into account factors, such as the dexterity or reach of the system.

The iterated search continues until an acceptable system topology is determined. When this occurs, the process 200 proceeds, and the adjusted topology, i.e., adjusted snare grasp positions, angles, etc. are passed, to step 222, where the snare configuration is changed. The process 200 then proceeds to step 214, where the snare tool motion is executed. The process 200 iterates back to the beginning at step 200 and repeats.

The process 200 can be repeated through every tool motion request received from the user until the procedure is completed. Additionally, this process 200, running continually, can be used to alert the user that he is approaching or has reached a position where further movement cannot be achieved in the current configuration. This can be accomplished, for example, by establishing a warning zone in simulation where the user is alerted when the tool position approaches within a predetermined distance of the simulated workspace boundary. This alert can be in real-time using measured tool positions or can be anticipatory using simulated tool/workspace models.

Kinematics Modeling

We model the flexible device and the snare needles using the Cosserat rod model in which we model each member of the parallel structure as an unshearable and inextensible Cosserat rod with a state vector that contain states defining its material position $p(s) \in R^3$, material orientation represented as a unit quaternion $q(s)$, internal force $n(s) \in R^3$, and internal moment $m(s) \in R^3$. The states vary as a function of scalar arc-length s along the rod's body, measured from a proximal reference.

The rod's position, orientation, internal force, and internal moment propagate in arc-length according to:

$$p' = q e_3 q^{-1} \quad q' = \tfrac{1}{2} q u$$

$$m' = n \times p'^{-1} \quad n' = -r$$

where $u \in R^3$ is angular rate-of-change of the rod's body reference frame expressed in the body frame, $r \in R^3$ and $l \in R^3$ are externally applied distributed forces and moments per unit rod length, and ' indicates derivative with respect to arc-length s. We assume that $r=0$ and $l=0$ in this paper.

The internal moment can be related to the angular rate of change by a linear constitutive law of the form:

$$m = q[K_m(u - u^*)] q^{-1}$$

where $K_m = \text{diag}(EI, EI, JG)$ maps bending and torsion to internal moment, E is the Young's modulus, G is the shear modulus, I is the second moment of area about the body $e_1$ and $e_2$ axes, and J is the polar area moment about the body $e_3$ axis. The vector $u^*$ is the rod's precurvature in its undeformed state as represented in the rod's undeformed body frame. For example, $u^* = 0$ for a straight rod.

The state of the system x is constructed by packing the rod states of each element of the parallel structure into a single vector:

$$x = [x_t \, x_1 \, \ldots \, x_n] \tag{1}$$

where $x_t$ is the Cosserat-rod states of the flexible device (i.e., backbone position and orientation, and internal force and moment), $x_1 \ldots x_n$ are the Cosserat-rod states of the snare needles. (Note that x is a column-vector but we express it in the form of (1) for compactness.)

The state vector $x(s)$ is a function of the arc-length parameter s, which is defined so that $s=0$ is at the proximal end of the flexible device and $s = \ell_t$ at the distal end of the flexible device ($\ell_t$ and $\ell_i$ are the lengths of flexible device and $i^{th}$ snare-needle, respectively). The flexible device and snare needle Cosserat-rod states are packed into x so that the corresponding physical location on the flexible device and snares at arc-length s is located at a distance of $\ell_t - s$ from the flexible device's distal end.

Figure 10:
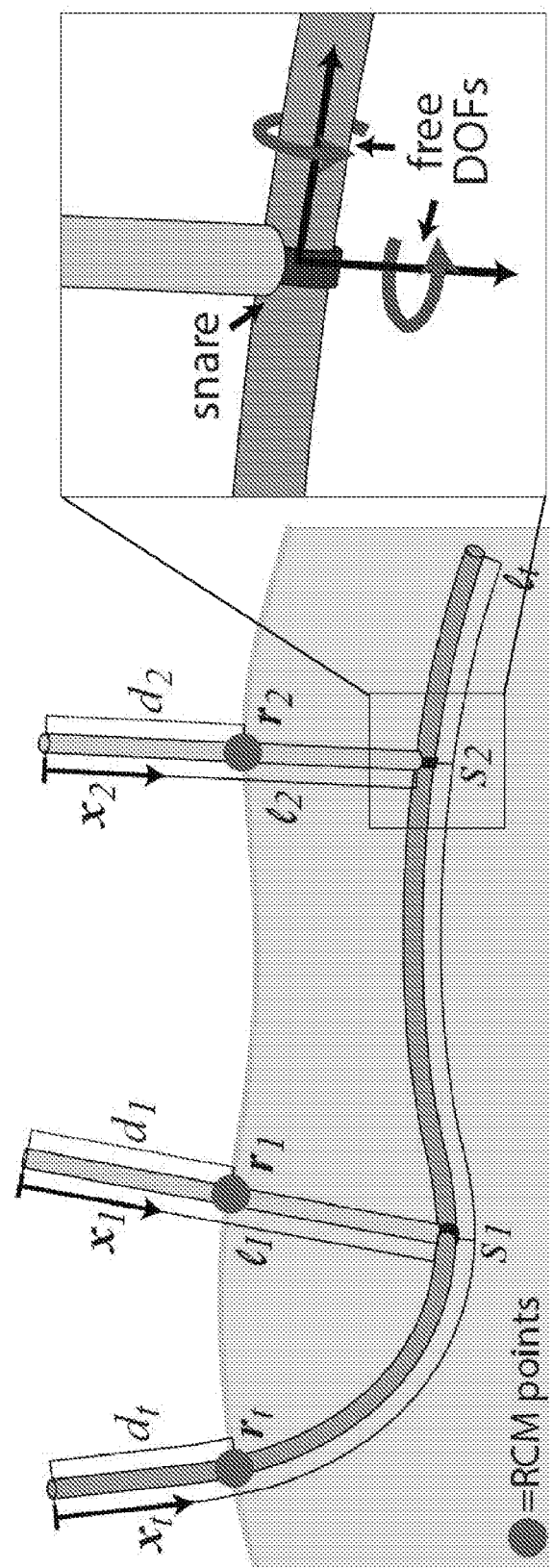
FIG. 10 illustrates a mechanics based model used to control the system.

FIG. 10 illustrates a mechanics-based model that predicts the arc-length states of the flexible device $x_t$ and snare needles, $x_1$ and $x_2$. The snares grasp the flexible device at the flexible device's arc-length $s_1$ and $s_2$. Remote centers of motion (RCM) of the flexible device and each snare is enforced at the RCM points $r_t$, $r_1$, and $r_2$. The unconstrained degrees of freedom permitted by the snare-grasp constraints expressed in (7).

The propagation of the state vector in arc-length s is governed by the arc-length derivative vector $$x' = [x_t' \, x_1' \, \ldots \, x_n'] = f(x, s) \tag{2}$$

The arc-length derivatives of the flexible device and the $i^{th}$ snare needle rod states are defined piecewise in arc-length as $$x_t'(s) = \begin{cases} [p_t' \, q_t' \, m_t' + \alpha \, n_t' + \beta], & \text{if } 0 \le s \le l_t \\ 0, & \text{otherwise} \end{cases} \tag{3}$$

$$x_i'(s) = \begin{cases} [p_i' \, q_i' \, m_i' \, n_i'], & \text{if } s_i - l_i \le s \le s_i \\ 0, & \text{otherwise} \end{cases} \tag{4}$$

and are given by the Cosserat-rod equations (13), where $s_i$ is the grasp location of the $i^{th}$ snare (FIG. 10).

The terms $\alpha(s) \in R^3$ and $\beta(s) \in R^3$ propagate the point loads applied to the flexible device by the snares toward the tool's distal end and are defined in arc-length as $$\alpha(s) = \sum_{i=1}^{n} \left( I - A_i A_i^\dagger \right) m_i \delta(s_i - s) \tag{5}$$

$$\beta(s) = \sum_{i=1}^{n} n_i \delta(s_i - s) \tag{6}$$

where $A_i(s) = [p_t'(s) \, p_i'(s)]$, $\delta(s)$ is the Dirac delta function, and † denotes the Moore-Penrose pseudoinverse. We model the snare grasps as unable to support moments about the flexible device and needle shaft directions ($p_t'$ and $p_i'$, i.e. the "Free DOFs" illustrated in FIG. 4). Equation (5) ensures that only the moment applied by each needle about the directions perpendicular to the flexible device and needle shafts is propagated toward the flexible device's distal end. Equation (6) propagates the point forces applied to the flexible device by the snares toward the flexible device's distal end. It is worth noting that these are assumptions. The free motion about the needle shaft is a good assumption, since the snare wire is free to move within the needle shaft. The free motion about the flexible device shaft is a good assumption if the coefficient of friction between the snare and the flexible device is low, but it is certainly possible to use materials that have higher frictional interaction for these components.

Figures 11A, 11B:
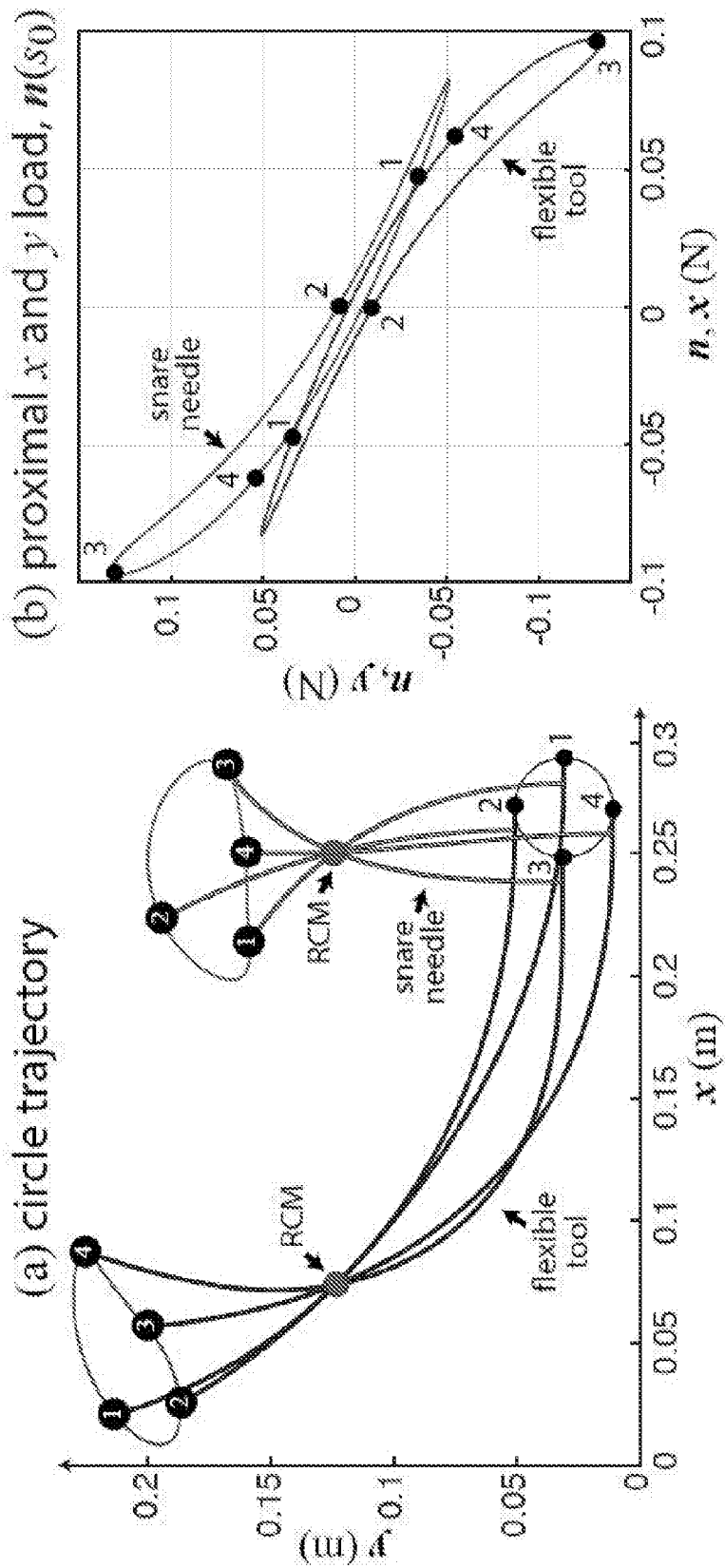
FIGS. 11A and 11B illustrate a portion of the system simulated using a mechanics based model.

FIG. 11A illustrates a simulated flexible device and a simulated single-snare robot following a 2-cm circle trajectory in the x-y plane while performing remote-center motion. A curve showing the proximal position of the flexible device and snare needle as the end-effector follows the circular trajectory is shown, with four configurations shown. FIG. 11B illustrates the proximal tension cycle of the flexible device and snare needle, which only lies in the x-y plane, required for the flexible device's end-effector to follow the circle trajectory.

Geometric and Wrench Constraints

Grasping the flexible device with the $i^{th}$ snare at arc-length location $s_i$ creates a state constraint that relates the components of the flexible device state $x_t(s_i)$ to the components of the snare needle's state $x_i(s_i)$. We approximate the geometric grasp interaction as a position constraint that enforces the tip of the needle to be coincident with the flexible device and a constraint that enforces the needle and flexible device shafts to be orthogonal. We assume the snare grasp cannot support moments in the $p_t'$ and $p_i'$ directions, which is enforced by two constraints on the snare needle's moment $m_t$. The geometric and wrench constraints can be represented for each of the n needles at arc-length $s_i$ as:

$$c_i(s_i) = \begin{bmatrix} p_t - p_i & \text{tip coincidence} \\ p_t' \cdot p_i' & \text{shaft orthogonality} \\ p_i' \cdot m_i & \text{needle shaft moment} \\ p_t' \cdot m_i & \text{tool shaft moment} \end{bmatrix} = 0 \quad (7)$$

We assume that the system is quasistatic which leads to constraints that enforce the force and moment at the flexible device's distal end to be balanced with any tip applied force F or moment T, represented by the tip constraint:

$$c_t(l_t) = \begin{bmatrix} m_t - T \\ n_t - F \end{bmatrix} = 0. \quad (8)$$

The n grasp constraints $c_i$ and the tip constraint $c_t$ can be packed into the combined constraint vector:

$$c = [c_t \, c_1 \, c_n] = 0. \quad (9)$$

Eight possible morphologies of a CRISP robot consisting of one flexible device and one to three snare needles. The flexible device and snares are highlighted in white for visibility.

Body Wall Fulcrum Constraints

Surgical robots that penetrate the skin perform remote-center motion (RCM) around a fulcrum, located at the body wall, that prevents the robot from pulling the patient's skin by minimizing the entry point's spatial motion [26]. An element of the CRISP system can perform remote-center motion around a virtual center. A member of the parallel structure passes through an RCM point r if there exists an arc-length d on its body such that the constraint:

$$c_{rcm} = p(d) - r = 0 \quad (10)$$

is satisfied as the CRISP robot moves. We denote the RCM points of the flexible device and snares to be $r_t$ and $r_1, \ldots, r_n$, respectively, with the arc-length position where the flexible device and snares intersect their RCM points denoted as $d_t$ and $d_1, \ldots, d_n$. The RCM constraint (10) can be incorporated into the kinematics framework for the flexible device and each of the snare needles by augmenting the system state x with the scalar arc-lengths $d_t$ and $d_1, \ldots, d_n$, and augmenting (9) with a constraint of the form (10) for the flexible device and each of the snare needles.

Forward and Inverse Kinematics

The forward kinematics of the parallel structure can be found by piecewise integrating (2) from arc-length $s_0 = \min\{0, s_1 - \ell_1, \ldots, s_n - \ell_n\}$ to arc-length $\ell_t$ with initial conditions $x(s_0) = x_0$. The initial condition vector $x_0$ is packed with a vector of inputs $u_0$, which are the initial positions and orientations of the flexible device and snare needles' proximal ends. The initial conditions are also packed with a vector $v_0$ containing the initial internal moments and forces of the flexible device and snare needles at their proximal ends, which are unknown a priori and must be solved for in order to satisfy the constraints (9). Given the known inputs $u_0$, we solved the forward kinematics using a numerical optimization routine that finds the unknowns $v_0$ that minimize PcP.

The inverse kinematics can be computed by augmenting the constraint vector (9) with a constraint on the flexible device's distal pose at arc-length $\ell_t$, of the form:

$$c_{inv}(l_t) = \begin{bmatrix} p_t - P \\ \log(q_t Q^{-1}) \end{bmatrix} = 0 \quad (11)$$

where P and Q denote the desired position and orientation, respectively. In this formulation of the inverse kinematics, the vector $v_0$ of unknowns includes the proximal pose of the flexible device and snare needles along with the proximal internal moments and forces. The same numerical optimization method can be used to solve the inverse and forward kinematics.

FIG. 11A shows the distal end of a hypothetical single-snare robot, with the flexible device and snare constructed out of Nitinol tubing with properties identical to the flexible device reported in Table 1, following a circular trajectory in the x-y plane with its heading pointing in the x direction and with RCM constraints illustrated. The necessary proximal flexible device and snare needle poses are computed by solving the inverse kinematics using the constraint (11). The flexible device and snare needle work in concert to position and orient the end-effector as shown. In all configurations, the flexible device and snare needles are antagonistic in that their proximal loads, which lie in the x-y plane, balance one another (FIG. 11B).

As noted in prior literature, the forward and inverse kinematics of elastic parallel and serial continuum manipulators may have more than one solution, where multiple vectors $v_0$ satisfy the constraints (9). This can occur in "buckled" configurations where multiple static equilibrium solutions exist that locally minimize the system's elastic potential energy. In this case, each of the buckled configurations can be found from the kinematic equations by appropriately selecting $v_0$. Elastic instability has been observed in other continuum devices, including concentric tube robots and has been explored for a robotic manipulation system that holds Kirchhoff elastic rods on both ends.

Reconfiguring the Snare Tool

Reconfiguration can be used to change the properties of a CRISP robot to satisfy changing application requirements; this distinguishes the system from other types of parallel continuum device devices. Here our system shares several key challenges with reconfigurable and parallel robot systems, notably the challenge of determining the optimal configuration/design for a given task. The system can be configured into a variety of morphologies in which the complexity increases with the number of flexible devices and snares. FIGS. 4A-4H illustrate some possible arrangements with one flexible device and from one to three snare tools 100. There are many possible morphologies whose utility varies depending on the task. A morphology like FIG. 4E could be used to control the flexible device's body along with its tip, while a morphology like that of FIG. 4F, where one snare grasps another, could be used to decrease a snare needle's compliance or exploit mechanical advantage.

It may be tempting to reduce the compliance by regrasping the flexible device with needles that are much stiffer than the flexible device. However, using snare needles that are much stiffer than the flexible device they manipulate reduces the system's ability to control tip orientation independently of the tip position. This is because the flexible device and snare needles work in concert to position and orient the tip, i.e., the flexible device bends the snare needles and vice versa as shown in the example of FIG. 5(a). When the snare needles are much stiffer than the flexible device, then the pose of the distal-most snare dominates the pose of the tip. This effect can be observed in the Jacobian's condition number. We anticipate that the compliance of a snared-tool system can be decreased without affecting the ability to control the tip pose by increasing the number (but not the stiffness) of snare needles.

Experimental Results

Five configurations compare the ground-truth magnetic tracker measurements of the flexible device's backbone position to that predicted by the kinematic model. Experiments were performed to verify the kinematic model by creating a system with two stainless steel snare tools and a superelastic Nitinol flexible device. Table 1 lists the system's parameters. The snares carried by the snare tools were constructed out of 1.52 mm wide, 0.28 mm thick superelastic Nitinol strip, and were tightened by hand. The configurations were similar in arrangement of the components to that illustrated in FIG. 4B, each having different orientations of the flexible device and snare tools.

TABLE 1

Parameters of the CRISP device.

| | Flexible Device | Snare Tool 1 | Snare Tool 2 |
|---|---|---|---|
| Outer Diameter (mm) | 1.02 | 3.00 | 3.00 |
| Inner Diameter (mm) | 0.84 | 2.30 | 2.30 |
| Length (mm) | 475 | 157 | 153 |
| Young's Modulus (GPa) | 50 | 180 | 180 |
| Poisson's Ratio | 0.33 | 0.305 | 0.305 |
| Grasp-Point Location (mm) | — | 207 | 434 |

A Northern Digital Inc. Aurora tabletop electromagnetic tracking system with a hand-held measurement probe was used to localize the base positions and orientations of the flexible device and the snare needles. We measured the grasp-point location of each snare on the flexible device by hand. Ground-truth measurements of the flexible device's backbone position were taken by manually sliding a 0.3 mm diameter electromagnetic sensor through the flexible device with the device placed in five configurations and comparing it to the backbone position predicted by the kinematic model. The ground-truth measurements are plotted on top of the predicted backbone position for all five experimental configurations.

Experimental testing has shown that there are snare tool and flexible device configuration where the kinematic equations have more than one solution. As described above in regard to the process 200 implemented by the system (see FIG. 9), the iteration loop 216 can search for the solution by appropriately selecting the initial moment and load (which are unique) at the proximal ends of the flexible device and snare needles. In the experiments, the numerical method was able to find multiple solutions by starting from two different initial values of the vector $v_0$.

Figure 12:
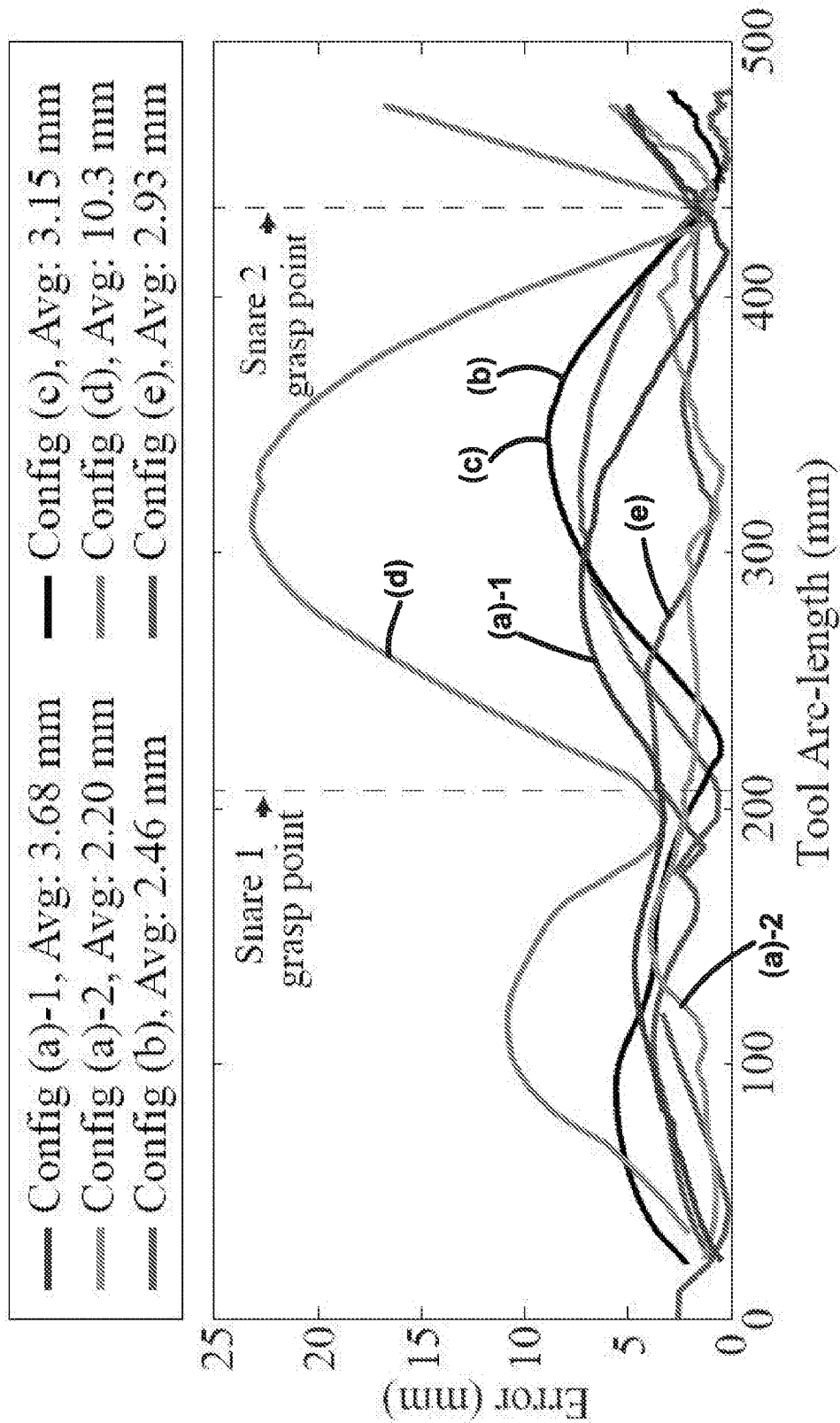
FIG. 12 is a chart illustrating backbone error between measured and simulated data during experimentation.

FIG. 12 shows the ground-truth error between the predicted flexible device backbone curve and the raw data obtained with the electromagnetic tracker for each of the experimental configurations. The error e(s) was computed at arc-length s as:

$$e(s) = \min_k \| p_t(s) - p_k^* \| \qquad (12)$$

where $p_t$ is the predicted backbone curve and $p^*k$ is a raw data point indexed by integer k=1, , , N and N is the number of gathered data points.

The average error for each configuration is shown in the legend of FIG. 6. The average error for all configurations except (d) was less than 4 mm. In the case of configuration (d), the average error was 10.3 mm, which we expect was caused by unmodeled static friction at the interface of the snare needles and flexible device. Static friction was dominated by the flexible device's internal moments and forces in the other configurations. When scaled by the shortest snare's length, the normalized error of configuration (d) was 6.7%.

FIG. 12 illustrates backbone error measured between the mechanics-based model and the raw tracker data for each experimental configuration. Error is shown as a function of the flexible device's backbone arc-length, with average backbone error in the legend. The arc-length locations (Table 1) where the snares grasp the flexible device are shown.

FIG. 12 shows that the flexible device's backbone error decreases near arc-lengths where the snare needles grasp the flexible device. This is a result of the snare needle's stiffness preventing it from deflecting under the loads applied by the flexible device. The model predicts the deflection, but using stiffer needles reduces uncertainty. This can be exploited by placing multiple grasp points along the flexible device's body, as FIG. 6 illustrates, to reduce the uncertainty of the predicted flexible device backbone curve by preventing errors at the proximal end from propagating down the flexible device's body. CRISP robots share this property with continuum and rigid-link parallel robots, whose structure prevents error in the individual joints from producing an amplified error at its end-effector.

The system 10 implementing the snare tool 100 is a novel approach to minimally-invasive medicine that reduces invasiveness by increasing the number of instruments that enter the body (in contrast to single-port approaches) while decreasing the diameter of each instrument down to that of a needle, requiring minimal or no incisions. The system 10 is an excellent candidate for a robotic approach since the necessary motion of the snare needles 100 and flexible device 20 outside the body is nonintuitive, particularly in the presence of body-wall fulcrum (i.e., RCM) constraints.

Reconfiguration is a unique aspect that makes the system 10 particularly versatile. An open problem that snare tools share with reconfigurable robots is that of planning when and how to reconfigure as task requirements change. Planning for reconfigurable robots includes both planning for individual components and planning the connectivity of the reconfigurable parts. In the context of the snare tool manipulator system 10 in the operating room, the planning problem includes both planning the motion of the system inside the body while incorporating anatomical and safety constraints, and determining what configurations the system should form itself into based on the surgeon's needs (e.g., what forces are needed at the end effector). The ability of the parallel structure of the snare tools 100 to reconfigure from stiff to compliant configurations can be important for certain surgical applications, such as those that require localizing tumors via palpation (e.g., in the lung or liver).

From the above description of the invention, those skilled in the art will perceive applications, improvements, changes and modifications to the invention. Such applications, improvements, changes and modifications within the skill of the art are intended to be covered by the appended claims.

The invention claimed is:

1. A snare tool manipulator system comprising:
an elongated flexible device having a length and including a distally mounted end effector configured to perform a task, the flexible device being operable to manipulate the end effector in order to perform the task, wherein the flexible device is configured to access a surgical site on a patient percutaneously through a first insertion site on the patient; and
an elongated snare tool comprising a distally mounted snare device configured for grasping the flexible device at a position along its length, the snare tool being operable robotically to manipulate the flexible device which in response manipulates the end effector, wherein the snare tool is configured to enter the patient percutaneously through a second insertion site on the patient, different than the first insertion site, to grasp the flexible device.

2. The system recited in claim 1, wherein the snare tool comprises a snare tube for delivering the snare device, the snare tool further comprising a snare actuating member that extends through an inner lumen of the snare tube and is actuatable to operate the snare device.

3. The system recited in claim 2, wherein the snare actuating member comprises a snare wire that extends through the inner lumen of the snare tube, the snare device comprising a looped portion of the snare wire, wherein the snare wire is actuatable to extend the snare loop from the distal end of the snare tube to receive the flexible device and retract the snare loop into the distal end of the snare tube.

4. The system recited in claim 2, wherein the snare device comprises at least one of a loop, a hook, and a grasper.

5. The system recited in claim 2, wherein the snare tube is configurable to include at least one of straight sections and curved sections.

6. The system recited in claim 2, wherein the snare tube is a needle-like structure having a diameter of 3.0 millimeters or less.

7. The system recited in claim 2, wherein the snare device comprises a loop and the snare tool is configured to position the loop for receiving the flexible device and permitting the flexible device to pass through the loop, the snare tool being actuatable to cause the loop to constrict onto and grasp the flexible device.

8. The system recited in claim 2, wherein the snare actuating member comprises a wire constructed of a material with shape memory properties and the snare device comprises a looped portion of the wire that has a predetermined shape, the looped portion being adapted to be compressed when it is passed through the inner lumen of the snare tube and to resume its predetermined shape when it exits through the distal end of the snare tube.

9. The system recited in claim 8, wherein the predetermined shape of the looped portion is one of a circular, elliptical, polygonal, and P shape.

10. The system recited in claim 1, wherein the snare tool is adapted to actuate the end effector of the flexible device by applying a rotational force to the end effector.

11. The system recited in claim 1, further comprising:
a snare tool actuator for robotically actuating the snare tool;
a flexible tool actuator for robotically actuating the flexible tool;
a controller programmed to control the snare tool actuator and flexible tool actuator according to received operator instructions in order to produce desired movement of the end effector on the distal end of the flexible tool; and
a user interface comprising a graphical user interface and a control input device, wherein the control input device is configured to provide the user instructions to the controller in response to control inputs from the user indicative of the desired movement of the end effector.

12. The system recited in claim 11, wherein the controller is programmed to:
implement a kinematic model to estimate a topology of the flexible tool and snare tool combination;
perform a calculation to determine the motion of the snare tool actuator and the flexible tool actuator necessary to produce the desired movement of the end effector indicated by the control inputs; and
actuate the snare tool actuator and flexible tool actuator to produce the desired movement of the end effector.

13. The system recited in claim 12, wherein the controller is further programmed to perform a simulation using the kinematic model to determine whether the desired movement of the end effector is possible with the current topology of the flexible tool and snare tool, and to adjust the configuration of the snare tool in order to produce a topology of the flexible tool and snare tool that will permit the desired movement of the end effector.

14. The system recited in claim 13, wherein the controller is programmed to iterate the determination of whether the desired movement of the end effector is possible and the adjustment of the configuration of the snare tool until a topology of the flexible tool and snare tool that will permit the desired movement of the end effector is determined.

15. The system recited in claim 12, wherein the controller is programmed to enforce a remote center of motion of the snare tool when actuating the snare tool actuator.

16. The system recited in claim 11, wherein the snare tool actuator comprises a robotic arm.

17. The system recited in claim 11, further comprising a tracking system for tracking the position and orientation of the snare tool and providing the tracked position and orientation to the controller.

18. The system recited in claim 11, wherein the flexible tool comprises a continuum device.

19. The system recited in claim 1, wherein the flexible device comprises a surgical device for percutaneously delivering the end effector to a worksite in order to perform a surgical task, and wherein the snare tool is configured for percutaneous insertion to grasp and manipulate the flexible device.

20. The system recited in claim 19, further comprising a snare tool actuator for robotically actuating the snare tool, wherein the snare tool actuator is configured to be static in position relative to the patient.

21. The system recited in claim 19, further comprising a snare tool actuator for robotically actuating the snare tool, wherein the snare tool actuator is adapted to have a dynamically controlled position so that is moves in response to patient movement in order to maintain a fixed position relative to the patient.

22. The system recited in claim 19, further comprising sensors for sensing the position of the snare tool relative to a predetermined location relative to the patient.

23. The system recited in claim 19, wherein the snare tool is configured to be patient mounted in order to maintain a fixed position relative to the patient.

24. A snare tool manipulator system comprising:

an elongated flexible device having a length and including a distally mounted end effector configured to perform a task, the flexible device being operable to manipulate the end effector in order to perform the task;

an elongated snare tool comprising a distally mounted snare device configured for grasping the flexible elongated member at a position along its length, the snare tool being operable robotically to manipulate the flexible device which in response manipulates the end effector;

a snare tool actuator for robotically actuating the snare tool;

a flexible tool actuator for robotically actuating the flexible tool;

a controller programmed to control the snare tool actuator and flexible tool actuator according to received operator instructions in order to produce desired movement of the end effector on the distal end of the flexible tool; and a user interface comprising a graphical user interface and a control input device, wherein the control input device is configured to provide the user instructions to the controller in response to control inputs from the user indicative of the desired movement of the end effector;

wherein the controller is programmed to:

implement a kinematic model to estimate a topology of the flexible tool and snare tool combination;

perform a calculation to determine the motion of the snare tool actuator and the flexible tool actuator necessary to produce the desired movement of the end effector indicated by the control inputs; and actuate the snare tool actuator and flexible tool actuator to produce the desired movement of the end effector.

\* \* \* \* \*